United States Patent
Watnick

(10) Patent No.: US 9,921,224 B2
(45) Date of Patent: *Mar. 20, 2018

(54) USE OF CD36 TO IDENTIFY CANCER SUBJECTS FOR TREATMENT

(71) Applicant: Children's Medical Center Corporation, Boston, MA (US)

(72) Inventor: Randolph S. Watnick, Newton, MA (US)

(73) Assignee: CHILDREN'S MEDICAL CENTER CORPORATION, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/773,596

(22) PCT Filed: Mar. 13, 2014

(86) PCT No.: PCT/US2014/026546
§ 371 (c)(1),
(2) Date: Sep. 8, 2015

(87) PCT Pub. No.: WO2014/151840
PCT Pub. Date: Sep. 25, 2014

(65) Prior Publication Data
US 2016/0033513 A1    Feb. 4, 2016

Related U.S. Application Data

(60) Provisional application No. 61/782,850, filed on Mar. 14, 2013.

(51) Int. Cl.
| | |
|---|---|
| *G01N 33/574* | (2006.01) |
| *C07K 5/12* | (2006.01) |
| *A61K 47/68* | (2017.01) |
| *C12Q 1/68* | (2018.01) |
| *A61K 38/17* | (2006.01) |
| *A61K 38/18* | (2006.01) |

(52) U.S. Cl.
CPC ... *G01N 33/57492* (2013.01); *A61K 38/1709* (2013.01); *A61K 38/18* (2013.01); *A61K 47/6811* (2017.08); *C07K 5/12* (2013.01); *C12Q 1/6886* (2013.01); *C12Q 2600/106* (2013.01); *C12Q 2600/158* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,696,080 A | 12/1997 | O'Brien et al. |
| 5,700,909 A | 12/1997 | O'Brien |
| 5,714,459 A | 2/1998 | O'Brien et al. |
| 6,500,431 B1 | 12/2002 | Gill |
| 7,166,691 B2 | 1/2007 | Koochekpour et al. |
| 7,341,730 B1 | 3/2008 | Gill |
| 2002/0177551 A1 | 11/2002 | Terman |
| 2004/0120961 A1 | 6/2004 | Koochekpour et al. |
| 2004/0175361 A1 | 9/2004 | Blaschuk et al. |
| 2004/0229799 A1 | 11/2004 | Qi |
| 2006/0275274 A1 | 12/2006 | Onichtchouk et al. |
| 2007/0099251 A1 | 5/2007 | Zhang et al. |
| 2009/0269373 A1 | 10/2009 | Qi |
| 2010/0144603 A1 | 6/2010 | Watnick |
| 2011/0271357 A1 | 11/2011 | Kim et al. |
| 2013/0072425 A1 | 3/2013 | Watnick |
| 2014/0113310 A9 | 4/2014 | Skolnick et al. |
| 2015/0320825 A1 | 11/2015 | Watnick |

FOREIGN PATENT DOCUMENTS

| | | | |
|---|---|---|---|
| WO | WO 95/03821 A1 | 2/1995 | |
| WO | WO1995025543 * | 9/1995 | ........... A61K 39/395 |
| WO | WO1996030332 * | 10/1996 | ........... C07C 229/36 |
| WO | WO 00/02902 A1 | 1/2000 | |
| WO | WO 02/24952 A1 | 3/2002 | |
| WO | WO 2004/084930 A1 | 10/2004 | |
| WO | WO 2004/096159 A2 | 11/2004 | |
| WO | WO 2005/073374 A1 | 8/2005 | |
| WO | WO 2007/047796 A2 | 4/2007 | |
| WO | WO 2007/047796 A3 | 4/2007 | |
| WO | WO 2007/066018 A2 | 6/2007 | |
| WO | WO 2009/002931 A2 | 12/2008 | |
| WO | WO 2010/105256 A1 | 9/2010 | |
| WO | WO 2011/084685 A2 | 7/2011 | |
| WO | WO 2013/096868 A2 | 6/2013 | |

OTHER PUBLICATIONS

Clezardin et al. Expression of thrombospondin (TSP1) and its receptors (CD36 and CD51) in normal, hyperplastic, and neoplastic human breast. Cancer Res. Mar. 15, 1993;53(6):1421-30.*

(Continued)

*Primary Examiner* — Satyanarayana R Gudibande
*Assistant Examiner* — Jia-Hai Lee
(74) *Attorney, Agent, or Firm* — Foley & Lardner LLP

(57) ABSTRACT

Provided herein are methods for identifying a subject with cancer for treatment with a Psap peptides. The subject is identified based on a level of CD36. Also provided herein are compositions and methods for treatment of a subject with cancer based on a level of CD36.

9 Claims, 8 Drawing Sheets

(56) References Cited

OTHER PUBLICATIONS

De Fraipont et al., Expression of the angiogenesis markers vascular endothelial growth factor-A, thrombospondin-1, and platelet-derived endothelial cell growth factor in human sporadic adrenocortical tumors: correlation with genotypic alterations. J Clin Endocrinol Metab. Dec. 2000;85(12):4734-41.
Doll et al., Thrombospondin-1, vascular endothelial growth factor and fibroblast growth factor-2 are key functional regulators of angiogenesis in the prostate. Prostate. Dec. 1, 2001;49(4):293-305.
Genbank Submission; NIH/NCBI, Accession No. EAW54436. Venter et al., Dec. 18, 2006. 3 pages.
Gopalakrishnan et al., Purified recombinant human prosaposin forms oligomers that bind procathepsin D and affect its autoactivation. Biochem J. Nov. 1, 2004;383(Pt. 3):507-15.
Hu et al., Prosaposin down-modulation decreases metastatic prostate cancer cell adhesion, migration, and invasion. Mol Cancer. Feb. 4, 2010;9:30.
Kalas et al., Oncogenes and Angiogenesis: down-regulation of thrombospondin-1 in normal fibroblasts exposed to factors from cancer cells harboring mutant ras. Cancer Res. Oct. 1, 2005;65(19):8878-86.
Kang et al., Prosaposin inhibits tumor metastasis via paracrine and endocrine stimulation of stromal p53 and Tsp-1. Proc Natl Acad Sci U S A. Jul. 21, 2009;106(29):12115-20. Epub Jul. 6, 2009. Erratum in: Proc Natl Acad Sci U S A. Sep. 8, 2009;106(36):15513.
Koochekpour et al., Amplification and overexpression of prosaposin in prostate cancer. Genes Chromosomes Cancer. Dec. 2005;44(4):351-64.
Koochekpour et al., Prosaposin is a novel androgen-regulated gene in prostate cancer cell line LNCaP. J Cell Biochem. Jun. 1, 2007;101(3):631-41.
Koochekpour et al., Prosaposin is an AR-target gene and its neurotrophic domain upregulates AR expression and activity in prostate stromal cells. J Cell Biochem. Aug. 15, 2008;104(6):2272-85.
Koochekpour, PSAP (prosaposin (variant Gaucher disease and variant metachromatic leukodystrophy)). Atlas Genet Cytogenet Oncol Haematol. 2007;10:370-384.
Lee et al., Saposin C promotes survival and prevents apoptosis via PI3K/Akt-dependent pathway in prostate cancer cells. Mol Cancer. Nov. 17, 2004;3:31.
Morimoto et al., Saposin A: second cerebrosidase activator protein. Proc Natl Acad Sci U S A. May 1989;86(9):3389-93.
O'Brien et al., Coding of two sphingolipid activator proteins (SAP-1 and SAP-2) by same genetic locus. Science. Aug. 26, 1988;241(4869):1098-101.
O'Brien et al., Saposin proteins: structure, function, and role in human lysosomal storage disorders. FASEB J. Mar. 1, 1991;5(3):301-8.
Panigone et al., Up-regulation of prosaposin by the retinoid HPR and the effect on ceramide production and integrin receptors. FASEB J. Jun. 2001;15(8):1475-7.
Qi et al., Functional human saposins expressed in *Escherichia coli*. Evidence for binding and activation properties of saposins C with acid beta-glucosidase. J Biol Chem. Jun. 17, 1994;269(24):16746-53.
Vogelstein et al., p53: The most frequently altered gene in human cancers. Nature education. 2010;3(9):6. Last accessed at http://www.nature.com/scitable/topicpage/p53-the-most-frequently-altered-gene-in-14192717 on Jul. 15, 2013.
Yabkowitz et al., Motility of human carcinoma cells in response to thrombospondin: relationship to metastatic potential and thrombospondin structural domains. Cancer Res. Jan. 15, 1993;53(2):378-87.
S. Wang et al: 11 Development of a prosaposin-derived therapeutic cyclic peptide that targets ovarian cancer via the tumor microenvironment 11, Science Translational Medicine, vol. 8, No. 329, Mar. 9, 2016.
European Search Report for EP 14770925.7 dated Nov. 8, 2016.
Kuemmerle, et al., "Lipoprotein Lipase Links Dietary Fat to Solid Tumor Cell Proliferation", Mol Cancer Ther; 10(3);427-36, Mar. 2011, AACR, Downloaded from mct.aacrjournals.org on May 17, 2017.
Office Action issued for CN 201480014414.8 dated Mar. 3, 2017 with English translation.

\* cited by examiner

USE OF CD36 TO IDENTIFY CANCER SUBJECTS FOR TREATMENT

CROSS-REFERENCE TO RELATED APPLICATIONS

This application is a national stage filing under 35 U.S.C. 371 of International Application PCT/US2014/026546, filed Mar. 13, 2014, which claims the benefit under 35 U.S.C. § 119(e) of the filing date of U.S. Provisional Application No. 61/782,850, filed Mar. 14, 2013, entitled "USE OF CD36 TO IDENTIFY CANCER SUBJECTS FOR TREATMENT", the entire contents of which are incorporated by reference herein in their entirety. International Application PCT/US2014/026546 was published under PCT Article 21(2) in English.

FEDERALLY SPONSORED RESEARCH OR DEVELOPMENT

This invention was made with U.S. Government support under R01CA135417 awarded by the National Cancer Institute. The U.S. Government has certain rights in the invention.

BACKGROUND OF INVENTION

Cancer remains a major public health priority. For example, an estimated 7.6 million deaths from cancer occurred in 2008. Treatments for cancer are constantly improving as technology and science progresses. Unfortunately, it has become apparent that many cancer therapeutics are effective only in subsets of cancer patients, even subsets of patients having the same type of cancer. As a result, it is becoming increasingly important to find ways to identify patients that are likely to respond to treatment.

SUMMARY OF INVENTION

Aspects of the disclosure are based in part on the discovery that elevated levels of CD36 in tumor cells indicate that a subject is responsive to or is likely to be responsive to treatment with a Psap peptide. Accordingly, aspects of the disclosure relate to methods for evaluating a subject's responsiveness to treatment with a Psap peptide by determining a level of CD36 in a sample, such as a tumor sample. In some embodiments, the methods described herein relate to identification or selection of a subject for treatment with a Psap peptide based on a level of CD36 in a sample. Other aspects of the disclosure relate to compositions and methods for treatment of a subject with cancer characterized by an elevated level of CD36.

In some aspects, the disclosure relates to a method for evaluating a subject's responsiveness to treatment with a Psap peptide, the method comprising determining a level of CD36 in a sample obtained from a subject having cancer, wherein an elevated level of CD36 in the sample compared to a control level indicates that the subject is responsive to or likely to be responsive to treatment with a Psap peptide. In some embodiments, the level of CD36 in the sample is determined by performing an assay. In some embodiments, the method further comprises identifying the subject with an elevated level of CD36 in the sample compared to the control level as responsive to or likely to be responsive to treatment with a Psap peptide. In some embodiments, the method further comprises administering to the subject identified as responsive to or likely to be responsive to treatment with a Psap peptide an effective amount of a Psap peptide to treat the cancer.

Other aspects of the disclosure relate to a method for treating a subject with cancer, the method comprising administering to a subject with cancer characterized by an elevated level of CD36 in a sample compared to a control level an effective amount of a Psap peptide to treat the cancer. In some embodiments, the control level is a level of CD36 from a non-cancerous cell or tissue obtained from the subject having the cancer. In some embodiments, the control level is a level of CD36 in a cell or tissue obtained from a healthy subject or a population of healthy subjects. In some embodiments, the control level is a predetermined level. In some embodiments, the level of CD36 is a CD36 protein level.

Further aspects of the disclosure relate to a method for treating a subject with cancer, the method comprising (a) selecting a subject with cancer on the basis that the subject is known to have an elevated level of CD36 in a sample compared to a control level; and (b) administering an effective amount of a Psap peptide to the subject because the subject has an elevated level of CD36 in the sample compared to the control level. In some embodiments, the control level is a level of CD36 from a non-cancerous cell or tissue obtained from the subject having the cancer. In some embodiments, the control level is a level of CD36 in a cell or tissue obtained from a healthy subject or a population of healthy subjects. In some embodiments, the control level is a predetermined level. In some embodiments, the level of CD36 is a CD36 protein level.

In some embodiments of any of the methods provided herein, the cancer is prostate cancer, breast cancer, ovarian cancer, lung cancer, leukemia, pancreatic cancer, glioblastoma multiforme, astrocytoma, or melanoma.

In some embodiments of any of the methods provided herein, the Psap peptide comprises the amino acid sequence CDWLPK (SEQ ID NO: 1), DWLPK (SEQ ID NO: 2), or DWLP (SEQ ID NO: 3), or an amino acid substitution variant thereof, wherein the amino acid substitution is:

a) Tyrosine (Y) for Tryptophan (W);
b) an amino acid substitution for Leucine (L) selected from Valine (V), Alanine (A) or Glycine (G), or a non-canonical amino acid of similar size, or a derivative thereof;
c) Arginine (R) for Lysine (K);
d) a D-isomer of Aspartic Acid (D) for an L-isomer of Aspartic Acid (D) and/or a D-isomer of Leucine (L) for a L-isomer of Leucine (L);
e) a D-isomer of Tryptophan (W) for an L-isomer of Tryptophan (W) and/or a D-isomer of Proline (P) for an L-isomer of Proline (P); or combinations thereof. In some embodiments, the Psap peptide is 50 amino acids or fewer in length. In some embodiments, the Psap peptide is 30 amino acids or fewer in length. In some embodiments, the Psap peptide is 15 amino acids or fewer in length. In some embodiments, the Psap peptide is 6 amino acids or fewer in length. In some embodiments, the Psap peptide is a cyclic peptide. In some embodiments, the non-canonical amino acid of similar size is methylvaline, methylleucine, or sarcosine.

In yet another aspect, the disclosure relates to a composition for use in treating a subject with cancer characterized by an elevated level of CD36 in a sample compared to a control level, the composition comprising a Psap peptide.

In another aspect, the disclosure relates to use of a composition for in the manufacture of a medicament for treating a subject with cancer characterized by an elevated level of CD36 in a sample compared to a control level, the composition comprising a Psap peptide.

In some embodiments of a use or composition provided herein, the control level is a level of CD36 from a non-cancerous cell or tissue obtained from the subject having cancer. In some embodiments of a use or composition provided herein, the control level is a level of CD36 in a cell or tissue obtained from a healthy subject or a population of healthy subjects. In some embodiments of a use or composition provided herein, the control level is a predetermined level. In some embodiments of a use or composition provided herein, the level of CD36 is a CD36 protein level.

In some embodiments of a use or composition described herein, the cancer is prostate cancer, breast cancer, ovarian cancer, lung cancer, leukemia, pancreatic cancer, glioblastoma multiforme, astrocytoma, or melanoma.

In some embodiments of a use or composition described herein, the Psap peptide comprises the amino acid sequence CDWLPK (SEQ ID NO: 1), DWLPK (SEQ ID NO: 2), or DWLP (SEQ ID NO: 3), or an amino acid substitution variant thereof, wherein the amino acid substitution is:

a) Tyrosine (Y) for Tryptophan (W);
b) an amino acid substitution for Leucine (L) selected from Valine (V), Alanine (A) or Glycine (G), or a non-canonical amino acid of similar size, or a derivative thereof;
c) Arginine (R) for Lysine (K);
d) a D-isomer of Aspartic Acid (D) for an L-isomer of Aspartic Acid (D) and/or a D-isomer of Leucine (L) for a L-isomer of Leucine (L);
e) a D-isomer of Tryptophan (W) for an L-isomer of Tryptophan (W) and/or a D-isomer of Proline (P) for an L-isomer of Proline (P); or combinations thereof. In some embodiments, the Psap peptide is 50 amino acids or fewer in length. In some embodiments, the Psap peptide is 30 amino acids or fewer in length. In some embodiments, the Psap peptide is 15 amino acids or fewer in length. In some embodiments, the Psap peptide is 6 amino acids or fewer in length. In some embodiments, the Psap peptide is a cyclic peptide. In some embodiments, the non-canonical amino acid of similar size is methylvaline, methylleucine, or sarcosine.

In some embodiments of a method, composition or use provided herein, the sample is a tumor sample.

DETAILED DESCRIPTION OF INVENTION

Figure 1A:
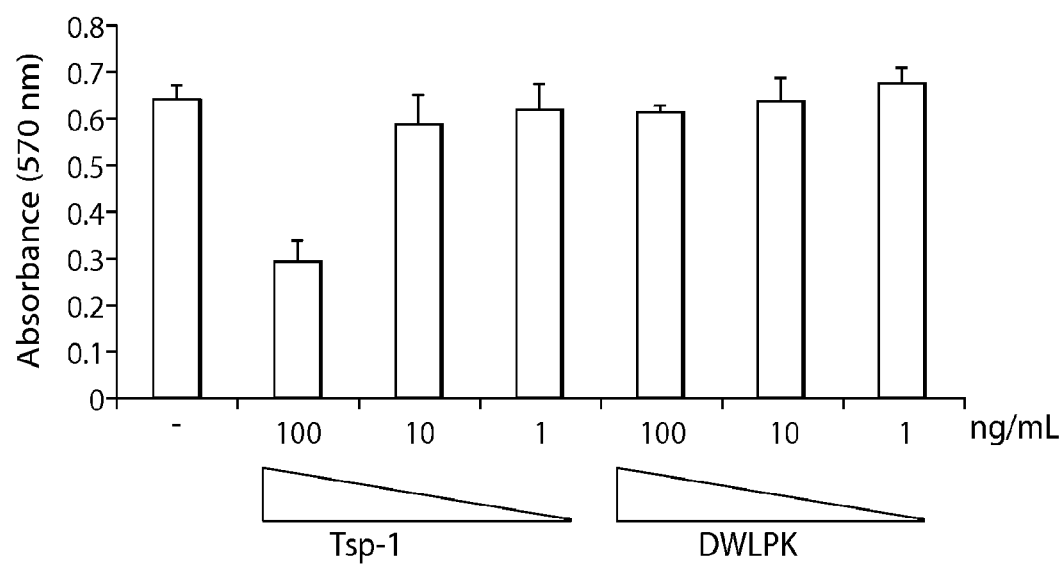
FIG. 1A is a graph showing proliferation of LLC cells 48 hours after additional of serially diluted amounts of recombinant Tsp-1 or DWLPK (SEQ ID NO: 2) peptide.

Psap peptides are therapeutic peptides containing amino acid sequences that were originally derived from fragments of Saposin A, a known anti-angiogenic protein. Psap peptides generally comprise a core sequence of CDWLPK (SEQ ID NO: 1), DWLPK (SEQ ID NO: 2), or DWLP (SEQ ID NO: 3) or an amino substitution variant thereof and can be of a length of as few as 4 amino acids (e.g., a peptide that consists of DWLP (SEQ ID NO: 3) or an amino acid substitution variant). Such Psap peptides have been shown previously to be effective for treating multiple types of cancers (see, e.g., PCT publications WO2009002931 and WO/2011/084685; PCT application PCT/US2012/71424, published as PCT publication WO/2013/096868, and U.S. patent application Ser. Nos. 12/640,788 and 13/516,511, all of which are incorporated herein by reference in their entirety). Administration of a Psap peptide was previously thought to stimulate thrombospondin (Tsp-1) in vivo, which in turn acted on endothelial cells causing an anti-angiogenic effect that resulted in indirect inhibition of cancer and/or metastatic growth.

As described herein, it has been discovered that tumor cells from several different types of cancers that are responsive Psap peptides express CD36. CD36 is a member of the class B scavenger receptor family of cell surface proteins and has many ligands including oxidized low density lipoprotein, oxidized phospholipids, long-chain fatty acids, collagen, and Tsp-1. Without wishing to be bound by any theory or mechanism, it is believed that administration of Psap peptide stimulates Tsp-1, which then acts directly on tumor cells by interacting with CD36 on the tumor cells. The interaction between Tsp-1 and CD36 on the tumor cells may result in inhibition of tumor cell proliferation and/or induction of tumor cell apoptosis. Thus, Psap peptides appear to treat cancer through two different independent mechanisms, indirectly through an anti-angiogenic affect and directly by interaction of Tsp-1 with CD36 on tumor cells. Thus, responsiveness of a subject with cancer to treatment with a Psap peptide may depend on the level of CD36 expressed by the cancer.

Accordingly, aspects of the disclosure relate to methods for evaluating a subject's responsiveness to treatment with a Psap peptide by determining a level of CD36 in a sample, such as a tumor sample. In some embodiments, the methods described herein relate to identification or selection of a subject for treatment with a Psap peptide based on a level of CD36 in a sample, such as a tumor sample. Other aspects of the disclosure relate to compositions and methods for treatment of a subject with cancer characterized by an elevated level of CD36 (e.g., selected or identified on the basis that the cancer has an elevated level of CD36 in a sample compared to a control level).

As used herein, "responsive to treatment with a Psap peptide" includes, but is not limited to, prevention or reduction of the development of a cancer, reduction of the symptoms of cancer, suppression or inhibition of the growth of a cancer, prevention of metastasis and/or invasion of an existing cancer, promotion or induction of regression of the cancer, inhibition or suppression of the proliferation of cancerous cells, reduction of angiogenesis and/or an increase in the amount of apoptotic cancer cells in response to treatment with a Psap peptide.

As used herein, "non-responsive to treatment with a Psap peptide" includes, but is not limited to, an absence of prevention or reduction of the development of a cancer, an absence of reduction of the symptoms of cancer, an absence of suppression or inhibition of the growth of a cancer, an absence of prevention of metastasis and/or invasion of an existing cancer, an absence of promotion or induction of regression of the cancer, an absence of inhibition or suppression of the proliferation of cancerous cells, an absence of reduction of angiogenesis and/or a decrease in the amount of apoptotic cancer cells in response to treatment with a Psap peptide.

Diagnostic and Theranostic Methods

Aspects of the disclosure relate to diagnostic and theranostic methods useful for evaluating a subject's responsiveness to treatment with a Psap peptide. In some embodiments, the method comprises determining a level of CD36 in a sample obtained from a subject having cancer, wherein an elevated level of CD36 in the sample compared to a control level indicates that the subject is responsive to or likely to be responsive to treatment with a Psap peptide (i.e., if the level of CD36 in the sample is elevated compared to a control level, the subject is identified as responsive or likely to be responsive to treatment with a Psap peptide). In some embodiments, the method further comprises identifying the subject with an elevated level of CD36 in the sample compared to the control level as responsive to or likely to be responsive to treatment with a Psap peptide. In some embodiments, the method further comprises administering to the subject identified as responsive to or likely to be responsive to treatment with a Psap peptide an effective amount of a Psap peptide described herein to treat the cancer. In some embodiments, the sample obtained from a subject having cancer is a tumor sample.

In some embodiments, an elevated level of CD36 in the sample compared to a control level indicates that the cancer will regress or is likely to regress in response to treatment with a Psap peptide. In some embodiments, the method further comprises identifying the subject with an elevated level of CD36 in the sample compared to the control level as having a cancer that will regress or is likely to regress in response to treatment with a Psap peptide. In some embodiments, the method further comprises administering to the subject identified having a cancer that will regress or is likely to regress in response to treatment with a Psap peptide an effective amount of a Psap peptide described herein to cause regression of the cancer.

As used herein, "an elevated level of CD36" means that the level of CD36 is above a control level, such as a pre-determined threshold or a level of CD36 in a control sample. Control levels are described in detail herein. An elevated level of CD36 includes a CD36 level that is, for example, 1%, 5%, 10%, 20%, 30%, 40%, 50%, 60%, 70%, 80%, 90%, 100%, 150%, 200%, 300%, 400%, 500% or more above a control level. An elevated level of CD36 also includes increasing a phenomenon from a zero state (e.g., no or undetectable CD36 expression in a control) to a non-zero state (e.g., some CD36 expression or detectable CD36 expression in a sample).

As used herein, "treatment with a Psap peptide" is meant to comprise administration of a Psap peptide to a subject. Psap peptides are described herein. It is to be understood that treatment with a Psap peptide may include treatment with only a Psap peptide or may include treatment with multiple agents or therapies, such as a Psap peptide and another chemotherapeutic agent and/or another form of therapy such as surgery, radiotherapy, or chemotherapy.

Treatment

Other aspects of the disclosure relate to methods for treating a subject with cancer. In some embodiments, the method comprises administering to a subject with cancer characterized by an elevated level of CD36 in a sample obtained from the subject compared to a control level an effective amount of a Psap peptide described herein to treat the cancer. In some embodiments, the method comprises:

(a) selecting a subject with cancer on the basis that the subject is known to have an elevated level of CD36 in a sample compared to a control level; and (b) administering an effective amount of a Psap peptide to the subject because the subject has an elevated level of CD36 in the sample compared to the control level.

Other aspects of the disclosure relate to compositions and uses of compositions in the manufacture of a medicament for treating a subject with cancer characterized by an elevated level of CD36 in a sample. In some embodiments, the composition comprises a Psap peptide as described herein. In some embodiments, the sample is a tumor sample.

As used herein, "treat" or "treatment" includes, but is not limited to, preventing or reducing the development of a cancer, reducing the symptoms of cancer, suppressing or inhibiting the growth of a cancer, preventing metastasis and/or invasion of an existing cancer, promoting or inducing regression of the cancer, inhibiting or suppressing the proliferation of cancerous cells, reducing angiogenesis and/or increasing the amount of apoptotic cancer cells. In some embodiments, treatment of cancer is a direct inhibition or suppression of the proliferation of cancer cells and does not involve an inhibition or suppression of angiogenesis (which indirectly leads to inhibition or suppression of the proliferation of cancer cells).

An effective amount is a dosage of the Psap peptide sufficient to provide a medically desirable result, such as treatment of cancer. The effective amount will vary with the particular cancer being treated, the age and physical condition of the subject being treated, the severity of the condition, the duration of the treatment, the nature of any concurrent therapy, the specific route of administration and the like factors within the knowledge and expertise of the health practitioner. For administration to a subject such as a human, a dosage of from about 0.001, 0.01, 0.1, or 1 mg/kg up to 50, 100, 150, or 500 mg/kg or more can typically be employed.

Psap peptides and compositions thereof can be formulated for a variety of modes of administration, including systemic, topical or localized administration. Techniques and formulations generally can be found in Remington's Pharmaceutical Sciences, Mack Publishing Co., Easton, Pa., latest edition. When administered, a Psap peptide may be applied in pharmaceutically-acceptable amounts and in pharmaceutically-acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A Psap peptide may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

A variety of administration routes are available. The particular mode selected will depend upon the type of cancer being treated and the dosage required for therapeutic efficacy. The methods of the disclosure, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion.

In some embodiments, administration is parenteral. Injectable preparations suitable for parenteral administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono or di glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

For topical administration, the pharmaceutical composition can be formulated into ointments, salves, gels, or creams, as is generally known in the art. Topical administration can utilize transdermal delivery systems well known in the art. An example is a dermal patch. Alternatively the biolistic gene gun method of delivery can be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The composition described herein can be coated on minute gold particles, and these coated particles are "shot" into biological tissues such as hemangiomas and melanoma under high pressure. An example of gene gun-based method is described for DNA based vaccination of cattle by Loehr B. I. et al., J. Virol. 2000, 74:6077-86.

The pharmaceutical compositions described herein are also suitably administered by intratumoral, peritumoral, intralesional or perilesional routes, to exert local as well as systemic effects. The intraperitoneal route is expected to be particularly useful, for example, in the treatment of ovarian tumors. For these uses, additional conventional pharmaceutical preparations such as tablets, granules, powders, capsules, and sprays can be preferentially required. In such formulations further conventional additives such as binding-agents, wetting agents, propellants, lubricants, and stabilizers can also be required.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The active ingredients and/or the pharmaceutical compositions ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

In some embodiments, administration of a Psap peptide may be combined with another therapy, such as a chemotherapy, radiation, and/or surgery.

CD36

CD36 (Cluster of Differentiation 36) is an integral membrane protein found on the surface of many cell types in vertebrate animals and is also known as FAT, GP4, GP3B, GPIV, CHDS7, PASIV, SCARB3, and BDPLT10. The Entrez Gene ID for human CD36 is 948. Exemplary human CD36 transcripts and proteins are below:

```
CD36 Transcript Variant 1
                                                            (SEQ ID NO: 4)
CTTTCAATTCCTCTGGCAACAAACCACACACTGGGATCTGACACTGTAGAGTGCTTTCTCTTCTCTTTT

TTTGGGGGGGGAGGGGTGTGGTTGCATATTTAAACTCTCACGCATTTATGTACTGAGGACTGCAGTG

TAGGACTTTCCTGCAGAATACCATTTGATCCTATTAAGAATTGTCCAAATGTTGGAGCATTTGATTGAA

AAATCCTTCTTAGCCATTTTAAAGATAGCTTTCCAATGATTAGACGAATTGATTCTTTCTGTGACTCAT

CAGTTCATTTCCTGTAAAATTCATGTCTTGCTGTTGATTTGTGAATAAGAACCAGAGCTTGTAGAAACC

ACTTTAATCATATCCAGGAGTTTGCAAGAAACAGGTGCTTAACACTAATTCACCTCCTGAACAAGAAAA

ATGGGCTGTGACCGGAACTGTGGGCTCATCGCTGGGGCTGTCATTGGTGCTGTCCTGGCTGTGTTTGGA

GGTATTCTAATGCCAGTTGGAGACCTGCTTATCCAGAAGACAATTAAAAAGCAAGTTGTCCTCGAAGAA

GGTACAATTGCTTTTAAAAATTGGGTTAAAACAGGCACAGAAGTTTACAGACAGTTTTGGATCTTTGAT

GTGCAAAATCCACAGGAAGTGATGATGAACAGCAGCAACATTCAAGTTAAGCAAAGAGGTCCTTATACG

TACAGAGTTCGTTTTCTAGCCAAGGAAAATGTAACCCAGGACGCTGAGGACAACACAGTCTCTTTCCTG

CAGCCCAATGGTGCCATCTTCGAACCTTCACTATCAGTTGGAACAGAGGCTGACAACTTCACAGTTCTC

AATCTGGCTGTGGCAGCTGCATCCCATATCTATCAAAATCAATTTGTTCAAATGATCCTCAATTCACTT

ATTAACAAGTCAAAATCTTCTATGTTCCAAGTCAGAACTTTGAGAGAACTGTTATGGGGCTATAGGGAT

CCATTTTTGAGTTTGGTTCCGTACCCTGTTACTACCACAGTTGGTCTGTTTTATCCTTACAACAATACT

GCAGATGGAGTTTATAAAGTTTTCAATGGAAAAGATAACATAAGTAAAGTTGCCATAATCGACACATAT

AAAGGTAAAAGGAATCTGTCCTATTGGGAAAGTCACTGCGACATGATTAATGGTACAGATGCAGCCTCA

TTTCCACCTTTTGTTGAGAAAAGCCAGGTATTGCAGTTCTTTTCTTCTGATATTTGCAGGTCAATCTAT

GCTGTATTTGAATCCGACGTTAATCTGAAAGGAATCCCTGTGTATAGATTTGTTCTTCCATCCAAGGCC

TTTGCCTCTCCAGTTGAAAACCCAGACAACTATTGTTTCTGCACAGAAAAAATTATCTCAAAAAATTGT

ACATCATATGGTGTGCTAGACATCAGCAAATGCAAAGAAGGGAGACCTGTGTACATTTCACTTCCTCAT

TTTCTGTATGCAAGTCCTGATGTTTCAGAACCTATTGATGGATTAAACCCAAATGAAGAAGAACATAGG

ACATACTTGGATATTGAACCTATAACTGGATTCACTTTACAATTTGCAAAACGGCTGCAGGTCAACCTA
```

-continued

```
TTGGTCAAGCCATCAGAAAAAATTCAAGTATTAAAGAATCTGAAGAGGAACTATATTGTGCCTATTCTT

TGGCTTAATGAGACTGGGACCATTGGTGATGAGAAGGCAAACATGTTCAGAAGTCAAGTAACTGGAAAA

ATAAACCTCCTTGGCCTGATAGAAATGATCTTACTCAGTGTTGGTGTGGTGATGTTTGTTGCTTTTATG

ATTTCATATTGTGCATGCAGATCGAAAACAATAAAATAAACCTGGCTCAAGCACAAACCAATTTGTGTT

GTTCTGATTCAATAATTGGTTTCTGGGTGGCCAATTCAGAAGAAGAGTGTACATGCTCAACAAATCCTA

GGCCCTGCATTCCTGTCATCCTCATCCGGGGGAAACACCATCATCCCAGTAGCTGCCCTATTCAACTGC

AACAGTCTCCAGGACCATCAGTATACTGCATTTCATGTGCACCAAATATTTTGAAAGACATTTATAAAT

AATTGGCTTATGACTCATATTTCTCTATGAATACCTTCATACAGCAGGTATAACTCTTTTCTTTATGGG

CTTAAATATTTTGTCACTGATCCTGCAAATGGACATCATTTTAGCACACTAGCGGTTTATATTTTAAGG

ACCTTCATTCTCTGTTCTGCACCTCTTCTGGAAATTGAGTAAATTTTGCTTTTTTTTTTTACTCAGTT

GCAACTTACGCTTGGCATCTTCAGAATGCTTTTCTAGCATTAAGAGATGTAAATGATAAAGGAATTATT

GTATGAAATATTACAAAGCGTAGACTATGCATTGTTATTCATTATAATATTTTTTGCTGTCATAATCGC

CTCATAAAGACAGGTTTCAACCATTAAAATATGTICTTCCTTAAATTCCTGTGCTTTTICTAGTTCCTC

TTGTGTCATAAAATGTTTATCCTAATTTTCTCTCTGAAGTATATTTTATCTGAATCCACATTTCTTTAT

AAATCCATAGTCCTTGCTGAAATATGCTTTCTAAATTTCTACCACTTTGTTCTAGGCTAATTTTTTAAG

CTAATTGGATGAAGAACAAAAAGACATTTGGTTTCATCCTTTACAGCAGTAGGACAATTGCAAAGGTTT

TTCCTTITTCATAAGGAGACACATTAATAGGTAACTCTGTTTCTTGAGCAGGGGTTCACTTATTCTGAG

AGCATTAGTTCTCCTAAAAAGCTCCAGCATAGAAAGGGAAGATAAACCAAATTCTAGCTTGTGTTTTAC

CCACAGAAGGATACAGGACAAAGGAATAGTAACTGGCCTGTTTGGATACTAAAATCGAAAATAACTTTT

AGCCTCCTCCTTATGATAGCCGCCAGAGTAAATGTTGAGCATTACTACAGAAAAGCCACAAACCAAGAA

TCTACCTGTTTGGAAAGATCTTTTGCATCTCTGAAGGTGCTTAAAGCATACTTAGTGCCTTTCCTTTTA

ACTGGGAAGATAAAAGAAGTATCTGTCCAAGATATTAATATGTAAGATAACATTGTAGACATGTTCTTC

TGATAATACAAGGTTTATTCTATTTGCATTAGGATATTTGTGGACATGTCCATCTAATATAAAGGAAAG

TTTTTTAATCATTGAGGCATGTAGGGCTGAGTTATATAATGTAGAAACTTCTAAAGATAATTGGATGAG

AATATACATATTGACCTGTATATTATGACTAATCATGACTCAGATCTTAATACAGGGATGATCTCATAG

CATTTAGATATCAGAAAAGGTTTTGACCTATATGTCTTTAATATTGTTTGAATACATGTATAATCTTTA

TCATTCCTCAGTGTTTCATTTCTCAAATTCTGTAAAAGGAATATAAGAGGAAAGACAATTCATATACAA

AGACAACGAGATTAAAAATATGCAGTAGGAAAAATAATTACTTAAGGGGAGATTTTTTTTACATGAAAT

CTGGGCTTTGGATGTGTGTGTGTGTGTGTGTGTGTGTGTGTGCACATATGCACTGTGGTGGGAGTGG

GGCAACTTGGGGAATATGTTACATGTGTGACTTTGTTTTGCCCTGGCGAAGTTAATGTTGTTCAGAAAG

GGTAAATGTTTGGACACTTGCAATTGCTCATGGATGAATTTATATGTTTTAGTCATAGAAAAATTGTAC

CCTTTGATAGAAGCACATTTTCTTTCCAAAGCTGGTTATTAACCACAGAATTATAGCAGGTATTCATAA

CTTAAGTTTGAAAATCAATAGCGTCTGCAAATGGATTAACAGATTAGAGAATCAACAGCATCGGAAAAT

AGGTTAATGCATATTGCTTCTAACAAGTGCATGAAGAAATAGAAGAAGCTATGTAGCTTTCAGTTCTGA

CAGAAAAGGGTGAAGGAGGGTATCATTTCAAGAAAAAAAATAGCTATCACGCAATGGTTATCTCTGAAA

ATATTTGTATTAAGATGTGTATACATGGCCAGGCATGGTGGCTCATGCCTGTAATCCCAGCACTTTGGG

AGGCAGGTGGATCACGAGGTCAGGAGATCAAGACCATCCTGGCCAACATGGTGAAACCTCATCTCTACT

AAAAATACAAAAATGAGCGGGGTGTGGTGGCCCATGCCTGTAGTCCCAGCTGCTCGGGAGACTGAATCT

CTTGAGCCTGGGAAGCAGAGGTTGCAGTGAACTGAGATCGCGTCACTGCACTCCAGCCTGGTGACAGAG

CGAGATTCCATCTCAAAAAAAAAAAACAGTATGCACGTACAAATTTCTTAACCTGTTATCAATGTCTGA

GCTACATAATTATCTTTCTAGTTGGAGTTTGTTTTAGGTGTGTACCAACTGACATTTCAGTTTTTCTGT
```

-continued

TTGAAGTCCAATGTATTAGTGACTCTGTGGCTGCTCTCTTCACCTGCCCCTTGTGGCCTGTCTACAATT

CTAAATGGATTTTGAACTCAATGTCGTCGCTTCTGGTTTCCTGCATATACCAATAGCATTACCTATGAC

TTTTTTTTTCCTGAGCTATTTTCACTGAGCTGAGCTAATGAACTAAAACTGAGTTATGTTTAATATTTG

TATCAAATACATAAAAGGAATACTGCTTTTTCCTTTTGTGGCTCAAAGGTAGCTGCATTTTAAAATATT

TGTGAAAATAAAAACTTTTGTTATTAGAAAAATGA

CD36 Transcript Variant 2

(SEQ ID NO: 5)
GAGGATGTCAATGGCTTTCAGATGTCAGGATAACCTTAAGGATAGATGAAGGGTTGAGAGCCTGTGCCT

CATTTCTGAGTTCTCAGCTGCTATGCCGTGGAAATCCTGTTTACTTTCTGCATCTGCTCCTGCAAGACT

CTGGAGCCAGTCTTGAGGTCCTACATCTCCGAAAGCAAGCTCTTCTAGAAGTTGATAGCTTTCCAATGA

TTAGACGAATTGATTCTTTCTGTGACTCATCAGTTCATTTCCTGTAAAATTCATGTCTTGCTGTTGATT

TGTGAATAAGAACCAGAGCTTGTAGAAACCACTTTAATCATATCCAGGAGTTTGCAAGAAACAGGTGCT

TAACACTAATTCACCTCCTGAACAAGAAAAATGGGCTGTGACCGGAACTGTGGGCTCATCGCTGGGGCT

GTCATTGGTGCTGTCCTGGCTGTGTTTGGAGGTATTCTAATGCCAGTTGGAGACCTGCTTATCCAGAAG

ACAATTAAAAGCAAGTTGTCCTCGAAGAAGGTACAATTGCTTTTAAAAATTGGGTTAAAACAGGCACA

GAAGTTTACAGACAGTTTTGGATCTTTGATGTGCAAAATCCACAGGAAGTGATGATGAACAGCAGCAAC

ATTCAAGTTAAGCAAAGAGGTCCTTATACGTACAGAGTTCGTTTTCTAGCCAAGGAAAATGTAACCCAG

GACGCTGAGGACAACACAGTCTCTTTCCTGCAGCCCAATGGTGCCATCTTCGAACCTTCACTATCAGTT

GGAACAGAGGCTGACAACTTCACAGTTCTCAATCTGGCTGTGGCAGCTGCATCCCATATCTATCAAAAT

CAATTTGTTCAAATGATCCTCAATTCACTTATTAACAAGTCAAAATCTTCTATGTTCCAAGTCAGAACT

TTGAGAGAACTGTTATGGGCTATAGGGATCCATTTTTGAGTTTGGTTCCGTACCCTGTTACTACCACA

GTTGGTCTGTTTTATCCTTACAACAATACTGCAGATGGAGTTTATAAAGTTTTCAATGGAAAAGATAAC

ATAAGTAAAGTTGCCATAATCGACACATATAAAGGTAAAAGGAATCTGTCCTATTGGGAAAGTCACTGC

GACATGATTAATGGTACAGATGCAGCCTCATTTCCACCTTTTGTTGAGAAAAGCCAGGTATTGCAGTTC

TTTTCTTCTGATATTTGCAGGTCAATCTATGCTGTATTTGAATCCGACGTTAATCTGAAAGGAATCCCT

GTGTATAGATTTGTTCTTCCATCCAAGGCCTTTGCCTCTCCAGTTGAAAACCCAGACAACTATTGTTTC

TGCACAGAAAAATTATCTCAAAAAATTGTACATCATATGGTGTGCTAGACATCAGCAAATGCAAAGAA

GGGAGACCTGTGTACATTTCACTTCCTCATTTTCTGTATGCAAGTCCTGATGTTTCAGAACCTATTGAT

GGATTAAACCCAAATGAAGAAGAACATAGGACATACTTGGATATTGAACCTATAACTGGATTCACTTTA

CAATTTGCAAAACGGCTGCAGGTCAACCTATTGGTCAAGCCATCAGAAAAAATTCAAGTATTAAAGAAT

CTGAAGAGGAACTATATTGTGCCTATTCTTTGGCTTAATGAGACTGGGACCATTGGTGATGAGAAGGCA

AACATGTTCAGAAGTCAAGTAACTGGAAAAATAAACCTCCTTGGCCTGATAGAAATGATCTTACTCAGT

GTTGGTGTGGTGATGTTTGTTGCTTTTATGATTTCATATTGTGCATGCAGATCGAAAACAATAAAATAA

GTAAGTATGTACCAAAAAATATTGCTTCAATAATATTAGCTTATATATTACTTGTTTTCACTTTATCAA

AGAGAAGTTACATATTAGGCCATATATATTTCTAGACATGTCTAGCCACTGATCATTTTAAATATAGG

TAAATAAACCTATAAATATTATCACGCAGATCACTAAAGTATATCTTTAATTCTGGGAGAAATGAGATA

AAAGATGTACTTGTGACCATTGTAACAATAGCACAAATAAAGCACTTGTGCCAAAGTTGTCCAAAAAA

CD36 Transcript Variant 3

(SEQ ID NO: 6)
CTTTCAATTCCTCTGGCAACAAACCACACACTGGGATCTGACACTGTAGAGTGCTTTCTCTTCTCTTTT

TTTGGGGGGGGAGGGGTGTGGTTGCATATTTAAACTCTCACGCATTTATGTACTGAGGACTGCAGTG

TAGGACTTTCCTGCAGAATACCATTTGATCCTATTAAGAATTGTCCAAATGTTGGAGCATTTGATTGAA

-continued

```
AAATCCTTCTTAGCCATTTTAAAGATAGCTTTCCAATGATTAGACGAATTGATTCTTTCTGTGACTCAT

CAGTTCATTTCCTGTAAAATTCATGTCTTGCTGTTGATTTGTGAATAAGAACCAGAGCTTGTAGAAACC

ACTTTAATCATATCCAGGAGTTTGCAAGAAACAGGTGCTTAACACTAATTCACCTCCTGAACAAGAAAA

ATGGGCTGTGACCGGAACTGTGGGCTCATCGCTGGGGCTGTCATTGGTGCTGTCCTGGCTGTGTTTGGA

GGTATTCTAATGCCAGTTGGAGACCTGCTTATCCAGAAGACAATTAAAAAGCAAGTTGTCCTCGAAGAA

GGTACAATTGCTTTTAAAAATTGGGTTAAAACAGGCACAGAAGTTTACAGACAGTTTTGGATCTTTGAT

GTGCAAAATCCACAGGAAGTGATGATGAACAGCAGCAACATTCAAGTTAAGCAAAGAGGTCCTTATACG

TACAGAGTTCGTTTTCTAGCCAAGGAAAATGTAACCCAGGACGCTGAGGACAACACAGTCTCTTTCCTG

CAGCCCAATGGTGCCATCTTCGAACCTTCACTATCAGTTGGAACAGAGGCTGACAACTTCACAGTTCTC

AATCTGGCTGTGGCAGCTGCATCCCATATCTATCAAAATCAATTTGTTCAAATGATCCTCAATTCACTT

ATTAACAAGTCAAAATCTTCTATGTTCCAAGTCAGAACTTTGAGAGAACTGTTATGGGGCTATAGGGAT

CCATTTTTGAGTTTGGTTCCGTACCCTGTTACTACCACAGTTGGTCTGTTTTATCCTTACAACAATACT

GCAGATGGAGTTTATAAAGTTTTCAATGGAAAAGATAACATAAGTAAAGTTGCCATAATCGACACATAT

AAAGGTAAAAGGAATCTGTCCTATTGGGAAAGTCACTGCGACATGATTAATGGTACAGATGCAGCCTCA

TTTCCACCTTTTGTTGAGAAAAGCCAGGTATTGCAGTTCTTTTCTTCTGATATTTGCAGGTCAATCTAT

GCTGTATTTGAATCCGACGTTAATCTGAAAGGAATCCCTGTGTATAGATTTGTTCTTCCATCCAAGGCC

TTTGCCTCTCCAGTTGAAAACCCAGACAACTATTGTTTCTGCACAGAAAAATTATCTCAAAAAATTGT

ACATCATATGGTGTGCTAGACATCAGCAAATGCAAAGAAGGGAGACCTGTGTACATTTCACTTCCTCAT

TTTCTGTATGCAAGTCCTGATOTTTCAGAACCTATTGATGGATTAAACCCAAATGAAGAAGAACATAGG

ACATACTTGGATATTGAACCTATAACTGGATTCACTTTACAATTTGCAAAACGGCTGCAGGTCAACCTA

TTGGTCAAGCCATCAGAAAAAATTCAAGTATTAAAGAATCTGAAGAGGAACTATATTGTGCCTATTCTT

TGGCTTAATGAGACTGGGACCATTGGTGATGAGAAGGCAAACATGTTCAGAAGTCAAGTAACTGGAAAA

ATAAACCTCCTTGGCCTGATAGAAATGATCTTACTCAGTGTTGGTGTGGTGATGTTTGTTGCTTTTATG

ATTTCATATTGTGCATGCAGATCGAAAACAATAAAATAAGTAAGTATGTACCAAAAAATATTGCTTCAA

TAATATTAGCTTATATATTACTTGTTTTCACTTTATCAAAGAGAAGTTACATATTAGGCCATATATATT

TCTAGACATGTCTAGCCACTGATCATTTTTAAATATAGGTAAATAAACCTATAAATATTATCACGCAGA

TCACTAAAGTATATCTTTAATTCTGGGAGAAATGAGATAAAAGATGTACTTGTGACCATTGTAACAATA

GCACAAATAAAGCACTTGTGCCAAAGTTGTCCAAAAAA
```

CD36 Transcript Variant 4

(SEQ ID NO: 7)
```
AAGTTGCTGAGACAAGGGAAGAGAGATGAGGAACCAGAGCTTGTAGAAACCACTTTAATCATATCCAGG

AGTTTGCAAGAAACAGGTGCTTAACACTAATTCACCTCCTGAACAAGAAAAATGGGCTGTGACCGGAAC

TGTGGGCTCATCGCTGGGGCTGTCATTGGTGCTGTCCTGGCTGTGTTTGGAGGTATTCTAATGCCAGTT

GGAGACCTGCTTATCCAGAAGACAATTAAAAAGCAAGTTGTCCTCGAAGAAGGTACAATTGCTTTTAAA

AATTGGGTTAAAACAGGCACAGAAGTTTACAGACAGTTTTGGATCTTTGATGTGCAAAATCCACAGGAA

GTGATGATGAACAGCAGCAACATTCAAGTTAAGCAAAGAGGTCCTTATACGTACAGAGTTCGTTTTCTA

GCCAAGGAAAATGTAACCCAGGACGCTGAGGACAACACAGTCTCTTTCCTGCAGCCCAATGGTGCCATC

TTCGAACCTTCACTATCAGTTGGAACAGAGGCTGACAACTTCACAGTTCTCAATCTGGCTGTGGCAGCT

GCATCCCATATCTATCAAAATCAATTTGTTCAAATGATCCTCAATTCACTTATTAACAAGTCAAAATCT

TCTATGTTCCAAGTCAGAACTTTGAGAGAACTGTTATGGGGCTATAGGGATCCATITTTGAGTTTGGTT

CCGTACCCTGTTACTACCACAGTTGGTCTGTTTTATCCTTACAACAATACTGCAGATGGAGTTTATAAA

GTTTTCAATGGAAAAGATAACATAAGTAAAGTTGCCATAATCGACACATATAAAGGTAAAAGGAATCTG
```

-continued

```
TCCTATTGGGAAAGTCACTGCGACATGATTAATGGTACAGATGCAGCCTCATTTCCACCTTTTGTTGAG

AAAAGCCAGGTATTGCAGTTCTTTTCTTCTGATATTTGCAGGTCAATCTATGCTGTATTTGAATCCGAC

GTTAATCTGAAAGGAATCCCTGTGTATAGATTTGTTCTTCCATCCAAGGCCTTTGCCTCTCCAGTTGAA

AACCCAGACAACTATTGTTTCTGCACAGAAAAAATTATCTCAAAAAATTGTACATCATATGGTGTGCTA

GACATCAGCAAATGCAAAGAAGGGAGACCTGTGTACATTTCACTTCCTCATTTTCTGTATGCAAGTCCT

GATGTTTCAGAACCTATTGATGGATTAAACCCAAATGAAGAAGAACATAGGACATACTTGGATATTGAA

CCTATAACTGGATTCACTTTACAATTTGCAAAACGGCTGCAGGTCAACCTATTGGTCAAGCCATCAGAA

AAAATTCAAGTATTAAAGAATCTGAAGAGGAACTATATTGTGCCTATTCTTTGGCTTAATGAGACTGGG

ACCATTGGTGATGAGAAGGCAAACATGTTCAGAAGTCAAGTAACTGGAAAAATAAACCTCCTTGGCCTG

ATAGAAATGATCTTACTCAGTGTTGGTGTGGTGATGTTTGTTGCTTTTATGATTTCATATTGTGCATGC

AGATCGAAAACAATAAAATAAGTAAGTATGTACCAAAAAATATTGCTTCAATAATATTAGCTTATATAT

TACTTGTTTTCACTTTATCAAAGAGAAGTTACATATTAGGCCATATATATTTCTAGACATGTCTAGCCA

CTGATCATTTTTAAATATAGGTAAATAAACCTATAAATATTATCACGCAGATCACTAAAGTATATCTTT

AATTCTGGGAGAAATGAGATAAAAGATGTACTTGTGACCATTGTAACAATAGCACAAATAAAGCACITG

TGCCAAAGTTGTCCAAAAAA

CD36 Transcript Variant 5
                                                          (SEQ ID NO: 8)
ATGACATTATTAGTTCTGCCACTGGTAGGCATTAGAAGCAAGAAAAGGGAGACGGACCGAGGAAGCCAC

TTTGGTGAAACAAAAAGAAAAGCATTTGTTTATTTAGAACGGGCAAAATGATACGTTTCAGTGGGTGTT

TTCTTTGTACTTTGATCTTTTTGTACTGATATTTAAGCTTCTGTTTTATGATCTCTTTCTAATGATAGA

ACCAGAGCTTGTAGAAACCACTTTAATCATATCCAGGAGTTTGCAAGAAACAGGTGCTTAACACTAATT

CACCICCTGAACAAGAAAAATGGGCTGTGACCGGAACTGTGGGCTCATCGCTGGGCTGTCATTGGTGC

TGTCCTGGCTGTGTTTGGAGGTATTCTAATGCCAGTTGGAGACCTGCTTATCCAGAAGACAATTAAAAA

GCAAGTTGTCCTCGAAGAAGGTACAATTGCTTTTAAAAATTGGGTTAAAACAGGCACAGAAGTTTACAG

ACAGTTTTGGATCTTTGATGTGCAAAATCCACAGGAAGTGATGATGAACAGCAGCAACATTCAAGTTAA

GCAAAGAGGTCCTTATACGTACAGAGTTCGTTTTCTAGCCAAGGAAAATGTAACCCAGGACGCTGAGGA

CAACACAGTCTCTTTCCTGCAGCCCAATGGTGCCATCTTCGAACCTTCACTATCAGTTGGAACAGAGGC

TGACAACTTCACAGTTCTCAATCTGGCTGTGGCAGCTGCATCCCATATCTATCAAAATCAATTTGTTCA

AATGATCCTCAATTCACTTATTAACAAGTCAAAATCTTCTATGTTCCAAGTCAGAACTTTGAGAGAACT

GTTATGGGCTATAGGGATCCATTTTTGAGTTTGGTTCCGTACCCTGTTACTACCACAGTTGGTCTGTT

TTATCCTTACAACAATACTGCAGATGGAGTTTATAAAGTTTTCAATGGAAAAGATAACATAAGTAAAGT

TGCCATAATCGACACATATAAAGGTAAAAGGAATCTGTCCTATTGGGAAAGTCACTGCGACATGATTAA

TGGTACAGATGCAGCCTCATTTCCACCTTTTGTTGAGAAAAGCCAGGTATTGCAGTTCTTTTCTTCTGA

TATTTGCAGGTCAATCTATGCTGTATTTGAATCCGACGTTAATCTGAAAGGAATCCCTGTGTATAGATT

TGTTCTTCCATCCAAGGCCTTTGCCTCTCCAGTTGAAAACCCAGACAACTATTGTTTCTGCACAGAAAA

AATTATCTCAAAAAATTGTACATCATATGGTGTGCTAGACATCAGCAAATGCAAAGAAGGGAGACCTGT

GTACATTTCACTTCCTCATTTTCTGTATGCAAGTCCTGATGTTTCAGAACCTATTGATGGATTAAACCC

AAATGAAGAAGAACATAGGACATACTTGGATATTGAACCTATAACTGGATTCACTTTACAATTTGCAAA

ACGGCTGCAGGTCAACCTATTGGTCAAGCCATCAGAAAAAATTCAAGTATTAAAGAATCTGAAGAGGAA

CTATATTGTGCCTATTCTTTGGCTTAATGAGACTGGGACCATTGGTGATGAGAAGGCAAACATGTTCAG

AAGTCAAGTAACTGGAAAAATAAACCTCCTTGGCCTGATAGAAATGATCTTACTCAGTGTTGGTGTGGT
```

```
GATGTTTGTTGCTTTTATGATTTCATATTGTGCATGCAGATCGAAAACAATAAAATAAGTAAGTATGTA

CCAAAAATATTGCTTCAATAATATTAGCTTATATATTACTTGTTTTCACTTTATCAAAGAGAAGTTAC

ATATTAGGCCATATATATTTCTAGACATGTCTAGCCACTGATCATTTTTAAATATAGGTAAATAAACCT

ATAAATATTATCACGCAGATCACTAAAGTATATCTTTAATTCTGGGAGAAATGAGATAAAAGATGTACT

TGTGACCATTGTAACAATAGCACAAATAAAGCACTTGTGCCAAAGTTGTCCAAAAAA
```

CD36 Protein
(SEQ ID NO: 9)
```
MGCDRNCGLIAGAVIGAVLAVFGGILMPVGDLLIQKTIKKQVVLEEGTIAFKNWVKTGTEVYRQFWIFD

VQNPQEVMMNSSNIQVKQRGPYTYRVRFLAKENVTQDAEDNTVSFLQPNGAIFEPSLSVGTEADNFTVL

NLAVAAASHIYQNQFVQMILNSLINKSKSSMFQVRTLRELLWGYRDPFLSLVPYPVTTTVGLFYPYNNT

ADGVYKVFNGKDNISKVAIIDTYKGKRNLSYWESHCDMINGTDAASFPPFVEKSQVLQFFSSDICRSIY

AVFESDVNLKGIPVYRFVLPSKAFASPVENPDNYCFCTEKIISKNCTSYGVLDISKCKEGRPVYISLPH

FLYASPDVSEPIDGLNPNEEEHRTYLDIEPITGFTLQFAKRLQVNLLVKPSEKIQVLKNLKRNYIVPIL

WLNETGTIGDEKANMFRSQVTGKINLLGLIEMILLSVGVVMFVAFMISYCACRSKTIK
```

Psap Peptide

Prosaposin (Psap) is the Saposin precursor protein made up of approximately 524-527 amino acids which includes a 16 amino acids signal peptide. The full-length precursor polypeptide undergoes co-translational glycosylation and modification in the endoplasmic reticulum and Golgi system to yield a 70-72 kDa precursor protein. After transport to the lysosome, cathepsin D participates in its proteolytic processing to yield intermediate molecular forms of 35 to 53 kDa and then to a 13-kDa glycoprotein and finally to the mature 8-11 kDa partially glycosylated forms of individual Saposin molecules (O'Brien J. S., and Kishimoto Y, The FASEB J., 5: 301-8, 1991; Kishimoto Y. et al., J. Lipid Res. 33:1255-67, 1992). Prosaposin is processed into 4 cleavage products: Saposins A, B, C, and D. The amino acid sequences of Psap preproprotein isoforms A, B, and C and the amino acid sequence of cleavage product Saposin A are below:

Psap Preproprotein Isoform A
(SEQ ID NO: 10)
```
MYALFLLASLLGAALAGPVLGLKECTRGSAVWCQNVKTASDCGAVKHCLQ

TVWNKPTVKSLPCDICKDVVTAAGDMLKDNATEEEILVYLEKTCDWLPKP

NMSASCKEIVDSYLPVILDIIKGEMSRPGEVCSALNLCESLQKHLAELNH

QKQLESNKIPELDMTEVVAPFMANIPLLLYPQDGPRSKPQPKDNGDVCQD

CIQMVTDIQTAVRTNSTFVQALVEHVKEECDRLGPGMADICKNYISQYSE

IAIQMMMHMQPKEICALVGFCDEVKEMPMQTLVPAKVASKNVIPALELVE

PIKKHEVPAKSDVYCEVCEFLVKEVTKLIDNNKTEKEILDAFDKMCSKLP

KSLSEECQEVVDTYGSSILSILLEEVSPELVCSMLHLCSGTRLPALTVHV

TQPKDGGFCEVCKKLVGYLDRNLEKNSTKQEILAALEKGCSFLPDPYQKQ

CDQFVAEYEPVLIEILVEVMDPSFVCLKIGACPSAHKPLLGTEKCIWGPS

YWCQNTETAAQCNAVEHCKRHVWN
```

Psap Preproprotein Isoform B
(SEQ ID NO: 11)
```
MYALFLLASLLGAALAGPVLGLKECTRGSAVWCQNVKTASDCGAVKHCLQ

TVWNKPTVKSLPCDICKDVVTAAGDMLKDNATEEEILVYLEKTCDWLPKP

NMSASCKEIVDSYLPVILDIIKGEMSRPGEVCSALNLCESLQKHLAELNH

QKQLESNKIPELDMTEVVAPFMANIPLLLYPQDGPRSKPQPKDNGDVCQD

CIQMVTDIQTAVRTNSTFVQALVEHVKEECDRLGPGMADICKNYISQYSE

IAIQMMMHMQDQQPKEICALVGFCDEVKEMPMQTLVPAKVASKNVIPALE

LVEPIKKHEVPAKSDVYCEVCEFLVKEVTKLIDNNKTEKEILDAFDKMCS

KLPKSLSEECQEVVDTYGSSILSILLEEVSPELVCSMLHLCSGTRLPALT

VHVTQPKDGGFCEVCKKLVGYLDRNLEKNSTKQEILAALEKGCSFLPDPY

QKQCDQFVAEYEPVLIEILVEVMDPSFVCLKIGACPSAHKPLLGTEKCIW

GPSYWCQNTETAAQCNAVEHCKRHVWN
```

Psap Preproprotein Isoform C
(SEQ ID NO: 12)
```
MYALFLLASLLGAALAGPVLGLKECTRGSAVWCQNVKTASDCGAVKHCLQ

TVWNKPTVKSLPCDICKDVVTAAGDMLKDNATEEEILVYLEKTCDWLPKP

NMSASCKEIVDSYLPVILDIIKGEMSRPGEVCSALNLCESLQKHLAELNH

QKQLESNKIPELDMTEVVAPFMANIPLLLYPQDGPRSKPQPKDNGDVCQD

CIQMVTDIQTAVRTNSTFVQALVEHVKEECDRLGPGMADICKNYISQYSE

IAIQMMMHMDQQPKEICALVGFCDEVKEMPMQTLVPAKVASKNVIPALEL

VEPIKKHEVPAKSDVYCEVCEFLVKEVTKLIDNNKTEKEILDAFDKMCSK

LPKSLSEECQEVVDTYGSSILSILLEEVSPELVCSMLHLCSGTRLPALTV

HVTQPKDGGFCEVCKKLVGYLDRNLEKNSTKQEILAALEKGCSFLPDPYQ

KQCDQFVAEYEPVLIEILVEVMDPSFVCLKIGACPSAHKPLLGTEKCIWG

PSYWCQNTETAAQCNAVEHCKRHVWN
```

Saposin A
(SEQ ID NO: 13)
```
SLPCDICKDVVTAAGDMLKDNATEEEILVYLEKTCDWLPKPNMSASCKEI

VDSYLPVILDIIKGEMSRPGEVCSALNLCES
```

Aspects of the disclosure relate to a Psap peptide and uses thereof. Psap peptides comprise sequences that were originally derived from fragments of Saposin A. It was shown previously that fragments of Saposin A consisting of as few as 4 amino acids, and variants of these fragments, had anti-angiogenic and anti-cancer activity. Psap peptides and methods of making Psap peptides are known in the art (see, e.g., PCT publications WO2009002931 and WO/2011/084685; PCT application PCT/US2012/71424, published as PCT publication WO/2013/096868, and U.S. patent application Ser. Nos. 12/640,788 and 13/516,511, all of which are incorporated herein by reference in their entirety).

In some embodiments, a Psap peptide comprises the amino acid sequence CDWLPK (SEQ ID NO: 1), DWLPK (SEQ ID NO: 2), or DWLP (SEQ ID NO: 3), or an amino acid substitution variant thereof, wherein the amino acid substitution is:

a) Tyrosine (Y) for Tryptophan (W);
b) an amino acid substitution for Leucine (L) selected from Valine (V), Alanine (A) or Glycine (G), or a non-canonical amino acid of similar size, or a derivative thereof;
c) Arginine (R) for Lysine (K);
d) a D-isomer of Aspartic Acid (D) for an L-isomer of Aspartic Acid (D) and/or a D-isomer of Leucine (L) for a L-isomer of Leucine (L);
e) a D-isomer of Tryptophan (W) for an L-isomer of Tryptophan (W) and/or a D-isomer of Proline (P) for an L-isomer of Proline (P); or combinations thereof. In some embodiments, a Psap peptide comprises the amino acid sequence CDWLPK (SEQ ID NO: 1), DWLPK (SEQ ID NO: 2), or DWLP (SEQ ID NO: 3).

It is to be understood that a Psap peptide can be of any length. In some embodiments, the Psap peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 33, 34, 35, 36, 37, 38, 39, 40, 45, 50, 55, 60, 65, 70, 75, 80, 85, 90, 95 or 100 or more amino acids in length. In some embodiments, the Psap peptide is 5, 6, 7, 8, 9, 10, 11, 12, 13, 14, 15, 16, 17, 18, 19, 20, 21, 22, 23, 24, 25, 26, 27, 28, 29, 30, 31, 32, 33, 33, 34, 35, 36, 37, 38, 39, 40, 45, 50, 55, 60, 65, 70, 75, 80, 85, 90, 95, 100, 200, 300, 400, 500 or fewer amino acids in length. In some embodiments, the Psap peptide is 4-500, 4-400, 4-300, 4-200, 4-100, 4-90, 4-80, 4-70, 4-60, 4-50, 4-40, 4-30, 4-25, 4-20, 5-500, 5-400, 5-300, 5-200, 5-100, 5-90, 5-80, 5-70, 5-60, 5-50, 5-40, 5-30, 5-25, 5-20, 6-500, 6-400, 6-300, 6-200, 6-100, 6-90, 6-80, 6-70, 6-60, 6-50, 6-40, 6-30, 6-25, or 6-20 amino acids in length.

It is to be understood that amino acids flanking the CDWLPK (SEQ ID NO: 1), DWLPK (SEQ ID NO: 2), or DWLP (SEQ ID NO: 3) may be the naturally flanking amino acids present in Saposin A or Prosaposin (e.g., LEKTCDWLPKPNMS (SEQ ID NO: 14), the underlined amino acids are the amino acids naturally flanking the DWLP (SEQ ID NO: 3) sequence in Saposin A). Accordingly, in some embodiments, the Psap peptide comprises the amino acid sequence DWLPKPNMS (SEQ ID NO: 15), CDWLPKPNM (SEQ ID NO: 16), TCDWLPKPN (SEQ ID NO: 17), KTCDWLPKP (SEQ ID NO: 18), EKTCDWLPK (SEQ ID NO: 19), LEKTCDWLP (SEQ ID NO: 20) or an amino acid substitution variant thereof wherein the substitution occurs in CDWLPK (SEQ ID NO: 1), DWLPK (SEQ ID NO: 2), or DWLP (SEQ ID NO: 3). Other examples of Psap peptides include without limitation, DWLPKPNMS (SEQ ID NO: 21), CDWLPKPNM (SEQ ID NO: 22), TCDWLPKPN (SEQ ID NO: 23), KTCDWLPKP (SEQ ID NO: 24), EKTCDWLPK (SEQ ID NO: 25), and LEKTCDWLP (SEQ ID NO: 26). Other Psap peptide examples include, without limitation, DWLPKPNM (SEQ ID NO: 27), CDWLPKPN (SEQ ID NO: 28), TCDWLPKP (SEQ ID NO: 29), KTCDWLPK (SEQ ID NO: 30), EKTCDWLP (SEQ ID NO: 31), DWLPKPN (SEQ ID NO: 32), CDWLPKP (SEQ ID NO: 33), TCDWLPK (SEQ ID NO: 34), KTCDWLP (SEQ ID NO: 35), DWLPKP (SEQ ID NO: 36), CDWLPK (SEQ ID NO: 1), TCDWLP (SEQ ID NO: 37), DWLPK (SEQ ID NO: 2), CDWLP (SEQ ID NO: 38), and DWLP (SEQ ID NO: 3).

It is also to be understood that amino acids flanking CDWLPK (SEQ ID NO: 1), DWLPK (SEQ ID NO: 2), or DWLP (SEQ ID NO: 3) need not be the naturally flanking amino acids present in Saposin A or Prosaposin, but can instead be any amino acid. Thus, a Psap peptide can include any number and identity of flanking amino acids. In some embodiments, the flanking amino acids may comprise an antibody or antibody Fc domain, serum transferrin or portions thereof, albumin, or transthyretin (see, e.g., G. M. Subramanian, (2007), Nature Biotechnology 25, 1411-141).

Psap peptides can be synthesized using any method known in the art. Exemplary methods of synthesis include, but are not limited to, recombinant synthesis, liquid-phase synthesis, Solid-phase synthesis, chemical ligation (see, e.g., Molecular Cloning: A Laboratory Manual, J. Sambrook, et al., eds., Third Edition, Cold Spring Harbor Laboratory Press, Cold Spring Harbor, New York, 2001; Current Protocols in Molecular Biology, F. M. Ausubel, et al., eds., John Wiley & Sons, Inc., New York; Schnolzer, M. A., P.; Jones, A.; Alewood, D.; Kent, S. B. H. (2007). "In Situ Neutralization in Boc-chemistry Solid Phase Peptide Synthesis". Int. J. Peptide Res. Therap. 13 (1-2): 31-44; Albericio, F. (2000). Solid-Phase Synthesis: A Practical Guide (1 ed.). Boca Raton: CRC Press. p. 848; and Nilsson B L, Soellner M B, Raines R T (2005). "Chemical Synthesis of Proteins". Annu. Rev. Biophys. Biomol. Struct. 34: 91-118; and U.S. Pat. Nos. 4,749,742, 4,794,150, 5,552,471, 5,637,719, 6,001,966, 7,038,103, 7,094,943, 7,176,282, and 7,645,858, the entirety of which are incorporated herein by reference).

In some embodiments, the Psap peptide may be modified, for example, through oligomerization or polymerization (e.g., dimers, trimer, multimers, etc.), modifications of amino acid residues or peptide backbone, cross-linking, cyclization, conjugation, pegylation, glycosylation, acetylation, phosphorylation, fusion to additional heterologous amino acid sequences (for example, an antibody or antibody Fc domain, serum transferrin or portions thereof, albumin, or transthyretin), or other modifications that substantially alter the stability, solubility, or other properties of the peptide while substantially retaining or enhancing therapeutic activity. Conjugation may be, e.g., to a polymer. Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation may be through a linker, e.g., a peptide or chemical linker. Methods of modifying peptides are well known in the art (see, e.g., U.S. Pat. Nos. 5,180,816, 5,596,078, 5,990,273, 5,766,897, 5,856, 456, 6,423,685, 6,884,780, 7,610,156, 7,256,258, 7,589,170 and 7,022,673, and PCT publication WO 2010/014616, the contents of which are incorporated herein by reference).

In some embodiments, the Psap peptide is a cyclic peptide. Cyclic peptides are polypeptide chains whose amino and carboxyl termini are linked together with a peptide bond or other covalent bond, forming a circular chain. In one embodiment, the peptide contains amino and carboxyl terminal cysteine amino acid residues. Cysteines facilitate S—S disulfide bond formation. In one embodiment, the peptide contains additional cysteine amino acid residues, wherein the cysteine amino acid residues are near the termini but not necessarily at the very end. In some embodiments, the cysteine amino acid residues are within the five amino acid residues of the termini of the peptide. Methods of design and synthesis of cyclic peptides are well known in the art, e.g. as described in U.S. Pat. Nos. 5,596,078; 5,990,273; 7,589,170 and U.S. Patent Application No. 20080287649.

In some embodiments, the Psap peptide is functionally modified to enhance stability. In some embodiments, the Psap peptide comprises an N-terminal acetyl group and/or a C terminal amide group. In some embodiments, the Psap peptide comprises an N-terminal acetyl group and a C terminal amide group. In some embodiments, the Psap peptide is Ac-dWlP-Amide or Ac-DWLP-Amide (Ac=acetyl group, lower case D and L indicate D-amino acids, SEQ ID NOs: 39 and 40, respectively). In some embodiments, chemical modifications to the Psap peptide include, but are not limited to the inclusion of, alkyl, alkoxy, hydroxyalkyl, alkoxyalkyl, alkoxycarbonyl, alkenyl, alkynyl, cycloalkyl, amino, alkylamino, aminoalkyl, dialkylamino, aminodialkyl, halogen, heteroatom, carbocycle, carbocyclyl, carbocyclo, carbocyclic, aryl, aralkyl, aralkoxy, aryloxyalkyl, heterocycle, heterocyclyl, heterocyclic, heteroaryl, and/or aliphatic groups.

Psap peptides also encompass peptidomimetics (e.g., D-peptides, β peptides and peptoids). The peptidomimetics utilized can encompass the entire length of the Psap peptide, or only a portion of the Psap peptide. Peptidomimetics may include, e.g., D-amino acids, reduced amide bonds for the peptide backbone, and non-peptide bonds to link the side chains, pyrrolinone and sugar mimetics. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptidomimetics are also described (see, for example, Smith et al., J. Am. Chem. Soc. 2000, 122, 11037-11038, which is incorporated herein by reference in its entirety). In some embodiments the Psap peptide is in the form of a peptoid (U.S. Pat. No. 5,811,387; Simon et al. Proceedings of the National Academy of Sciences USA, (1992), 89(20), 9367-9371). In some embodiments, peptoids are poly-N-substituted glycines. In peptoids the side chain is connected to the nitrogen of the peptide backbone, instead of the α-carbon as in peptides. In some embodiments the peptoid contains nitroaromatic monomer units (Fowler et al., J Org Chem. 2009 Feb. 20; 74(4):1440-9). In some embodiments, the peptoid is N-substituted with alpha-chiral aromatic side chains (Gorske et al., J Am Chem Soc. 2006 Nov. 8; 128(44):14378-87) at one or more residues. In some embodiments, the Psap peptide comprises a peptoid region (i.e., containing one or more side chains connected to the nitrogen of the peptide backbone) and a peptide region (i.e., containing one or more side chains connected to the α-carbon).

Psap Amino Acid Substitutions

In some embodiments, a Psap peptide comprises an amino acid substitution variant of CDWLPK (SEQ ID NO: 1), DWLPK (SEQ ID NO: 2), or DWLP (SEQ ID NO: 3), wherein the amino acid substitution is:

a) Tyrosine (Y) for Tryptophan (W);
b) an amino acid substitution for Leucine (L) selected from Valine (V), Alanine (A) or Glycine (G), or a non-canonical amino acid of similar size, or a derivative thereof;
c) Arginine (R) for Lysine (K);
d) a D-isomer of Aspartic Acid (D) for an L-isomer of Aspartic Acid (D) and/or a D-isomer of Leucine (L) for a L-isomer of Leucine (L);
e) a D-isomer of Tryptophan (W) for an L-isomer of Tryptophan (W) and/or a D-isomer of Proline (P) for an L-isomer of Proline (P); or combinations thereof.

Conservative amino acid substitutions can be replacement of one amino acid residue with an amino acid residue having a side chain with a similar charge, size, polarity, hydrophobicity, or combination thereof. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Conservative amino acid substitutions typically do not change the overall structure of the peptide and/or the type of amino acid side chains available for forming van der Waals bonds with a binding partner. In some embodiments, a conservative substitution for Leucine is Valine. In some embodiments, a conservative substitution for Leucine is Valine or Alanine.

In some embodiments, conservative or non-conservative substitutions for Leucine are contemplated. In some embodiments, the substitution for Leucine is Valine, Glycine or Alanine. In some embodiments, a substitution for Leucine is Glycine. In some embodiments, a substitution for Leucine is Glycine or Valine. In some embodiments, the amino acid substitution is a Tyrosine (Y) for a Tryptophan (W).

Exemplary amino acid substitution variants include, but are not limited to, DWAP (SEQ ID NO: 41), DYLPK (SEQ ID NO: 42), DWVPK (SEQ ID NO: 43), DWLPR (SEQ ID NO: 44), DWAPK (SEQ ID NO: 45), and DYLP (SEQ ID NO: 46).

Substitution with a non-canonical amino acid is also contemplated herein. In some embodiments, Leucine is substituted with a non-canonical amino acid. In some embodiments, the non-canonical amino acid substitute for Leucine has a similar size to Leucine, Valine, Alanine, or Glycine. Examples of non-canonical amino acids include azidoalanine, azidohomoalanine, azidonorvaline, azidonorleucine, azidonorvaline, homoallyglycine, homopropargylcine, norvaline, norleucine, cis-crotyiglycine, trans-crotylglycine, 2-aminoheptanoic acid, 2-butynyiglycine, allyglycine, 3-(1-naphthyl)alanine, 3-(2-naphthyl)alanine, p-ethynyl-phenylalanine, p-propargly-oxy-phenylalanine, m-ethynyl-phenylalanine, 3-(6-chloroindolyl)alanine, 3-(6-bromoindolyl)alanine, 3-(5-bromoindolyl)alanine, azidohomoalanine, homopropargylglycine, p-chlorophenylalanine, α-aminocaprylic acid, methylvaline, methylleucine, or sarcosine. In some embodiments, Leucine is substituted with a non-canonical amino acid selected from methylvaline, methylleucine, or sarcosine. Non-canonical amino acids and methods of synthesis thereof are well known in the art (see, e.g., U.S. Patent Publications 2010-0247433, 2008-0214439, 2004-0053390, and 2004-0058415; PCT publication WO 03/073238; and U.S. Pat. No. 6,586,207, all of which are incorporated herein by reference).

Amino acid substitution can be achieved during chemical synthesis of the peptide by adding the desired substitute amino acid at the appropriate sequence in the synthesis process. Alternatively, molecular biology methods can be used. Non-conservative substitutions are also encompassed to the extent that they substantially retain the activities of those peptides described herein.

As previously described, Psap peptides comprising CDWLPK (SEQ ID NO: 1), DWLPK (SEQ ID NO: 2), or DWLP (SEQ ID NO: 3) having D-amino acid substitutions were also shown to have a desired therapeutic activity (see PCT application PCT/US2012/71424, published as PCT publication WO/2013/096868). As such, amino acid substitution variants resulting from substitution of one or more D-amino acids for the like L-amino acid are contemplated herein. In some embodiments, one D-amino acid substitution is present. In some embodiments, 2 or more D-amino acid substitutions are present. In some embodiments, 3, 4, or 5 D-amino acid substitutions are present. In some embodiments, the D-amino acid substitutions are evenly spaced, e.g., every other amino acid, of the 4-6 mer. In some embodiments, the D-amino acid substitution is for Tryptophan (W) and/or Proline (P). In some embodiments, the D-amino acid substitution is for Aspartic Acid (D) and/or Leucine (L)). The L and D convention for amino acid configuration refers not to the optical activity of the amino acid itself, but rather to the optical activity of the isomer of glyceraldehyde from which that amino acid can, in theory, be synthesized (D-glyceraldehyde is dextrorotary; L-glyceraldehyde is levorotary). Exemplary D amino acid substitutions include dWlP and DwLp (lower case D and L indicate D-amino acids, SEQ ID NOs: 47 and 48, respectively).

Assay

Aspects of the disclosure relate to performing an assay to determine a level of CD36 in a sample. Any assay known in the art can be used for measuring a CD36 level (see, e.g., Molecular Cloning: A Laboratory Manual, J. Sambrook, et al., eds., Third Edition, Cold Spring Harbor Laboratory Press, Cold Spring Harbor, New York, 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons, Inc., New York). The level of CD36 can be an mRNA level and/or a protein level. In some embodiments, the level of CD36 is a protein level. Assays for detecting CD36 mRNA include, but are not limited to, Northern blot analysis, RT-PCR, sequencing technology, RNA in situ hybridization (using e.g., DNA or RNA probes to hybridize to RNA molecules present in the sample), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer) with addressable locations, such as an Affymetrix microarray (Affymetrix®, Santa Clara, Calif.)). Methods for designing nucleic acid binding partners, such as probes, are well known in the art. In some embodiments, the nucleic acid binding partners bind to a part of or an entire nucleic acid sequence of CD36, the sequence being identifiable with the CD36 sequences provided herein.

Assays for detecting CD36 protein levels include, but are not limited to, immunoassays (also referred to herein as immune-based or immuno-based assays, e.g., Western blot, immunohistochemistry and ELISA assays), Mass spectrometry, and multiplex bead-based assays. Such assays for protein level detection are well-known in the art. Binding partners for protein detection can be designed using methods known in the art and as described herein. In some embodiments, the CD36 protein binding partners, e.g., anti-CD36 antibodies, bind to a part of or an entire amino acid sequence of the CD36 protein. Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329.

In some embodiments, the sample obtained from a subject is a tumor biopsy and the assay for detecting CD36 protein levels is an immuno-based assay performed on the tumor biopsy.

Any suitable binding partner for CD36 is contemplated for detection of a CD36 level. In some embodiments, the binding partner is any molecule that binds specifically to a CD36 protein. As described herein, "binds specifically to a CD36 protein" means that the molecule is more likely to bind to a portion of or the entirety of a CD36 protein than to a portion of or the entirety of a non-CD36 protein. In some embodiments, the binding partner is an antibody or antigen-binding fragment thereof, such as Fab, F(ab)2, Fv, single chain antibodies, Fab and sFab fragments, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Binding partners also include other peptide molecules and aptamers that bind specifically to CD36. Methods for producing peptide molecules and aptamers are well known in the art (see, e.g., published US Patent Application No. 2009/0075834, U.S. Pat. Nos. 7,435,542, 7,807,351, and 7,239,742).

Commercially available CD36 antibodies include, for example, N-15, $SM_\varphi$, L-17, ME542, H300, 185-1G2, and V-19 from Santa Cruz Biotechnology (Catalog numbers sc-5522, sc-7309, sc-13572, sc-5523, sc-9154, sc-21772, and sc-7641, respectively), JC63.1, FA6-152, and anti-CD36 from Abcam (Catalog numbers ab23680, ab17044, and ab78054, respectively).

In some embodiments, the binding partner is any molecule that binds specifically to a CD36 mRNA. As described herein, "binds specifically to a CD36 mRNA" means that the molecule is more likely to bind to a portion of or the entirety of the CD36 mRNA (e.g., by complementary base-pairing) than to a portion of or the entirety of a non-CD36 mRNA or other non-CD36 nucleic acid. In some embodiments, the binding partner that binds specifically to a CD36 mRNA is a nucleic acid, e.g., a probe. Binding partners can be designed using the nucleotide and amino acid sequences of CD36, which are provided herein. In some embodiments, a CD36 binding partner may comprise a detectable label, such as an enzymatically active group, a fluorescent molecule, a chromophore, a luminescent molecule, a specifically bindable ligand, or a radioisotope. In some embodiments, a second binding partner specific for the CD36 binding partner is also contemplated, such as a secondary antibody.

Sample

Aspects of the disclosure relate to determining a level of CD6 in a sample obtained from a subject. In some embodiments, the sample obtained from a subject is a tumor sample. As used herein, a tumor sample may comprise, e.g., a tumor cell, a population of tumor cells, a fragment of a tumor (e.g., a biopsy), or an entire tumor. In some embodiments, the tumor sample is a tumor biopsy. In some embodiments, the tumor sample comprises circulating tumor cells. In some embodiments, the tumor sample comprises ascites. In some embodiments, the tumor sample comprises pleural fluid. The tumor sample may contain non-tumor cells or non-tumor tissue (e.g., a biopsy that contains normal tissue surrounding a tumor fragment). In some embodiments, the sample may be a tissue or fluid sample obtained from a subject. Examples of fluid samples are blood, plasma, serum, and urine.

Subjects

Aspects of the disclosure relate to subjects, such as human subjects, with cancer. Any type of cancer is contemplated herein, including, but not limited to, leukemias, lymphomas, myelomas, carcinomas, metastatic carcinomas, sarcomas, adenomas, nervous system cancers and genitourinary cancers. Exemplary cancer types include adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor.

In some embodiments, the cancer is prostate cancer, breast cancer, ovarian cancer, lung cancer, leukemia, pancreatic cancer, glioblastoma multiforme, astrocytoma or melanoma. In some embodiments, the cancer is prostate cancer, breast cancer, lung cancer, leukemia, pancreatic cancer, glioblastoma multiforme, astrocytoma or melanoma. In some embodiments, the cancer is pancreatic cancer, ovarian cancer, breast cancer, prostate cancer, melanoma cancer, or lung cancer.

Control and Control Level

Aspects of the disclosure relate to comparison of a CD36 level in a sample with a control level. In some embodiments, the control level is a level of CD36 in a cell, tissue or fluid obtained from a healthy subject or population of healthy subjects. As used herein, a healthy subject is a subject that is apparently free of disease and has no history of disease, such as cancer.

In some embodiments, the control level is determined from a sample obtained from a subject having cancer. Accordingly, in some embodiments the control level is obtained from the same subject from whom the sample is obtained. In some embodiments, a control level is a level of CD36 from a non-cancerous cell or tissue obtained from the subject having the cancer.

In some embodiments, a control level is a level of CD36 that is undetectable or below a background/noise level obtained using standard methods of detection (e.g., Western blot or immunohistochemistry).

The disclosure also involves comparing the level of CD36 in a sample from the subject with a predetermined level or value, such that a control level need not be measured every time. The predetermined level or value can take a variety of forms. It can be single cut-off value, such as a median or mean. It can be established based upon comparative groups, such as where one defined group is known not to respond to treatment with a Psap peptide and another defined group is known to be responsive to treatment with a Psap peptide. It can be a range, for example, where the tested population is divided equally (or unequally) into groups, such as a unresponsive to treatment with a Psap peptide, somewhat responsive to treatment with a Psap peptide, and highly responsive to treatment with a Psap peptide, or into quadrants, the lowest quadrant being subjects with no response to treatment with a Psap peptide and the highest quadrant being subjects with the highest response to treatment with a Psap peptide response.

The predetermined value can depend upon the particular population selected. For example, an apparently healthy (no detectable cancer and no prior history of cancer) will have a different 'normal' range of CD36 than will a population the members of which have cancer but are known not to respond to treatment with a Psap peptide. Accordingly, the predetermined values selected may take into account the category in which a subject falls. Appropriate ranges and categories can be selected with no more than routine experimentation by those of ordinary skill in the art.

EXAMPLES

Example 1

Methods

Cell Lines and Primary Cells

The cell line PC3 was previously described (Kang et al. PNAS. 2009; 106:12115-20). PC3 cells were cultured in RPMI with 10% FBS. Human breast cancer cell lines MDA-MB-231 and MCF-7 were described previously (Ryu et al. PLoS one, 6, 2011). The murine Lewis lung carcinoma cell line LLCs (provided by Lea Eisenbach, Wiesmann Institute of Science, Rehovot, Israel) stably expressing RFP and firefly luciferase (Gupta G P, Massague J. Cancer metastasis: building a framework. Cell. 2006; 127:679-95; Gao D, Nolan D J, Mellick A S, Bambino K, McDonnell K, Mittal V. Endothelial progenitor cells control the angiogenic switch in mouse lung metastasis. Science. 2008; 319:195-8; and Joyce J A, Pollard J W. Microenvironmental regulation of metastasis. Nat Rev Cancer. 2009; 9:239-52), was cultured in DMEM supplemented with 10% fetal bovine serum. B16 melanoma cells, LNCaP prostate cancer cells, AsPc1 pancreatic cancer cells, and ID8 ovarian cancer cells were previously described (Overwijk W W et al. B16 as a mouse model for human melanoma. Curr Protoc Immunol. 2001, May; Chapter 20:Unit 20.1; Horoszewicz J S, Leong S S, Kawinski E et al. LNCaP model of human prostatic carcinoma. Cancer Res. 1983, April; 43(4):1809-18.; Chen W H, et al. Human pancreatic adenocarcinoma: in vitro and in vivo morphology of a new tumor line established from ascites. In Vitro 18: 24-34, 1982; and Roby K F, et al. Development of a syngeneic mouse model for events related to ovarian cancer. Carcinogenesis. 2000, 21:585-591). Primary ovarian cancer cells were derived from ovarian cancer patient ascites.

Western Blot Analysis

Cells were homogenized in lysis buffer (BioRad) containing protease inhibitors (Roche Applied Science). Samples were boiled in 1×SDS sampling buffer, and loaded onto 4-20% gradient Bis-Tris NuPAGE gels (Invitrogen). Western blotting was performed using antibodies specific for CD36 (AbCam, ab78054) or β-actin (Sigma-Aldrich).

In Vitro Cell Proliferation Assays

Cell proliferation was measured using the MTT (3-{4,5-Dimethylthiazol-2-yl}-2,5-diphenyltetrazolium bromide, Sigma-Aldrich) assay. Cells were seeded in 50 uL growth medium in 96 well culture plates and allowed to attach overnight. 50 uL of growth medium plus two-fold concentrated treatment reagents were then added. After each treatment time point, 10 uL of 5% MTT solution (buffered in PBS) was added to each well. Plates were incubated for an additional 4 h at 37° C. to allow MTT to be metabolically converted into formazan crystals at cell mitochondria. The formazan crystals were finally solubilized by adding 100 ul of 10% Sodium Dodecyl Sulphate in 50% N—N-Dimethylformamide to each microplate well. Absorbances at 550 and 680 nm (corresponding to formazan salt and reference wavelengths, respectively) were measured using a colorimetry microplate reader. Wells containing only complete medium were used as controls. Each experiment was performed twice, using six replicates for each drug concentration.

Results

Figure 1B:
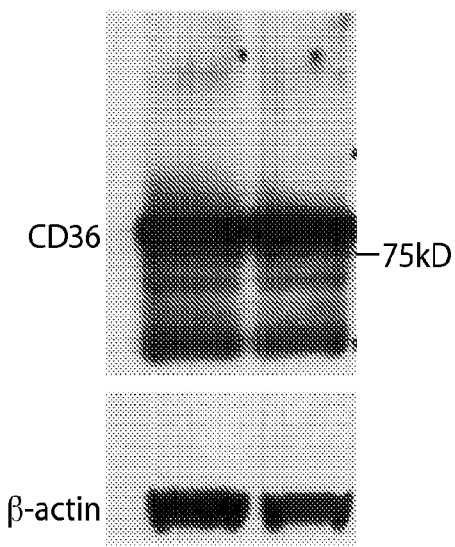
FIG. 1B is a photograph of a western blot showing that CD36 protein is expressed in LLC cells.

It was hypothesized that Tsp-1 upregulated by a Psap peptide may be acting directly on the cancer cells, rather than only through an indirect anti-angiogenic mechanism. To test this, LLC cells were treated with either recombinant Tsp-1 or DWLPK (SEQ ID NO: 2) Psap peptide and cell proliferation was measured using an MTT assay. It was found that Tsp-1 was capable of decreasing cell proliferation, while the Psap peptide did not affect cell proliferation (FIG. 1A). This supports the hypothesis that Tsp-1 can act directly on cancer cells, as this assay was performed in vitro in the absence of any blood vessels. These results also show that the Psap peptide alone does not appear affect cancer cell proliferation, supporting the hypothesis that Psap peptides may indirectly treat cancer through upregulation of Tsp-1. LLC cells were shown to express CD36, a receptor for Tsp-1, indicating that Tsp-1 may act directly on cancer cells through CD36 (FIG. 1B).

Figure 2:
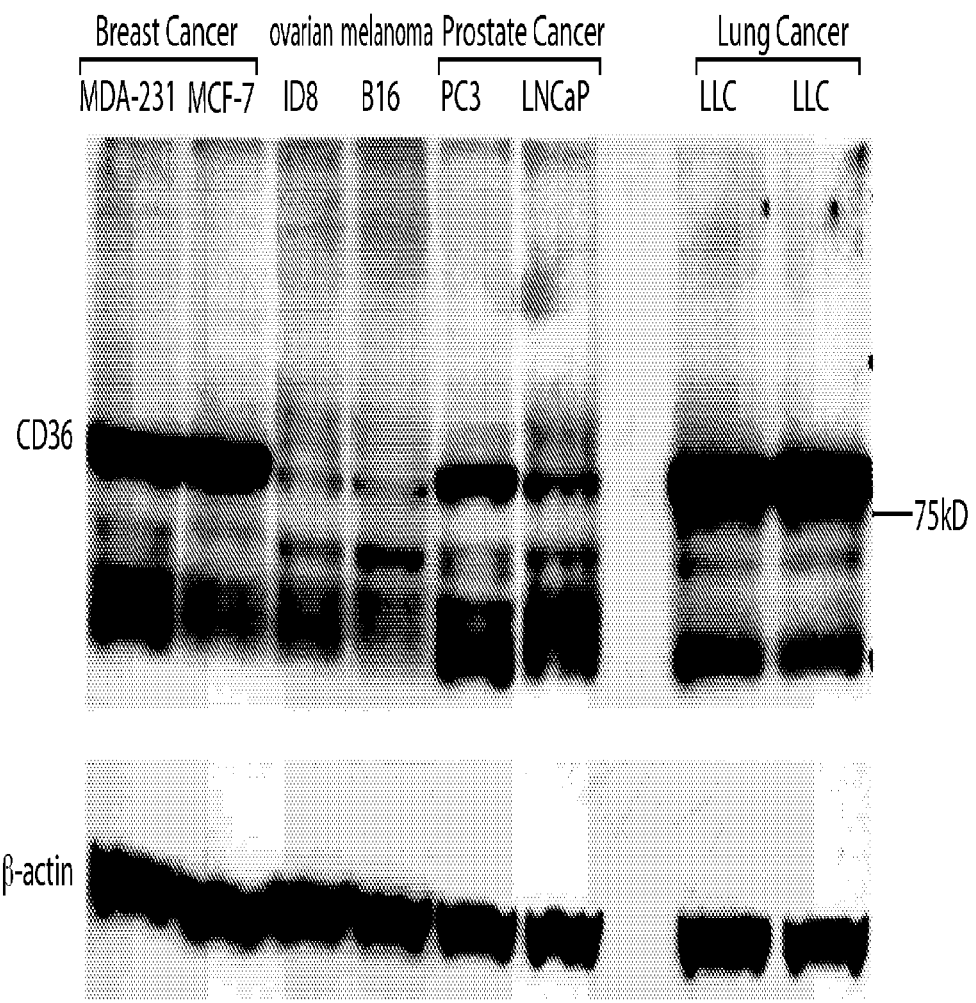
FIG. 2 is a photograph of a western blot showing that CD36 protein is expressed in breast cancer (MDA-231, MCF-7), ovarian cancer (ID8), melanoma (B16), prostate cancer (PC3 and LNCaP), and lung cancer (LLC) cell lines.

CD36 levels were measured in other cell lines to see if CD36 was also expressed by other cancer types. CD36 levels were measured in breast cancer (MDA-231, MCF-7), ovarian cancer (ID8), melanoma (B16), prostate cancer (PC3 and LNCaP), and lung cancer (LLC) cell lines by western blot analysis. It was found that CD36 protein was detectable in all cell lines tested, with particularly high levels of CD36 detectable in MDA-231, MCF-7, PC3, and LLC cell lines (FIG. 2). MDA-231, ID8, B16, PC3, and LLC cells have been shown previously to respond to Treatment with a Psap peptide in vivo.

The pancreatic cell line AsPc1 was also examined and found to express CD36.

Figure 3:
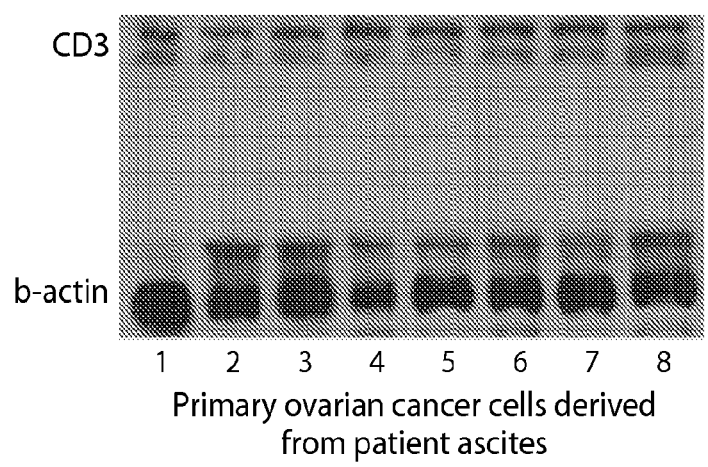
FIG. 3 is a photograph of a western blot showing that CD36 protein is expressed in primary ovarian cancer cell derived from patient ascites.
Figure 4:
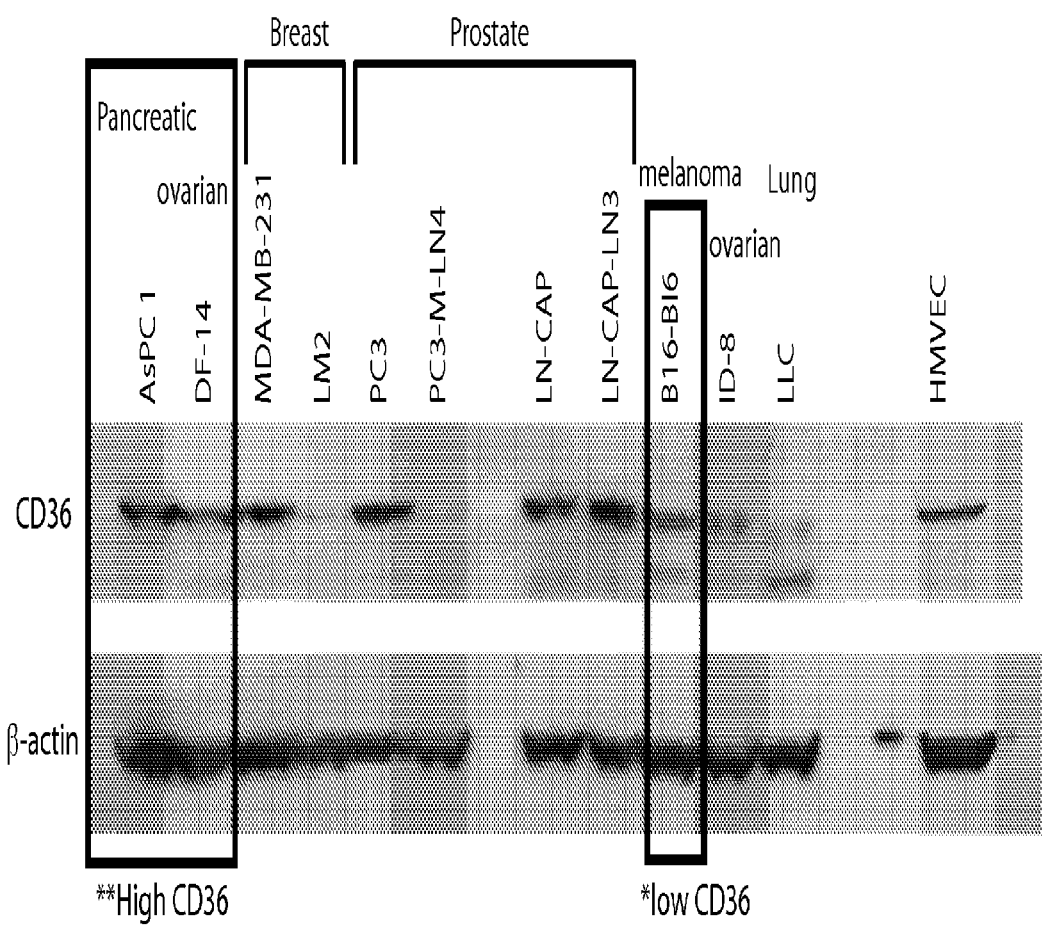
FIG. 4 is a photograph of a western blot showing that CD36 protein is expressed in pancreatic (AsPC1), ovarian (DF-14 and ID-8), breast (MDA-MB231 and LM2), prostate (PC3, PC3-M-LN4, LN-CAP, and LN-CAP-LN3), melanoma (B16-B16), and lung cancer (LLC) cells. Exemplary high and low CD36 expressing cells lines are shown in boxes.

CD36 levels were also measured in primary ovarian cancer cells derived from patients with ascites. CD36 protein was detectable in all primary ovarian cancer cells tested (FIG. 3).

Example 2

Methods

Mice and Cell Lines

All animal work is conducted in accordance with a protocol approved by the Institutional Animal Care and Use Committee. Wild type C57BL/6J, and GFP transgenic C57BL/6-Tg (ACTB-EGFP) 1 Osb/J are obtained from The Jackson Laboratory (Bar Harbor, Me.). CB-17 SCID mice are obtained from Charles River (Wilmington, Mass.).

The cell lines PC3 and PC3M-LN4 are previously described (14). Human breast cancer cell lines MDA-MB-231 and MDA-MB-LM2 are described previously (Ryu et al. PLoS one, 6, 2011). The murine Lewis lung carcinoma cell line LLCs/D122 (provided by Lea Eisenbach, Wiesmann Institute of Science, Rehovot, Israel) stably expressing RFP and firefly luciferase (Gupta G P, Massague J. Cancer metastasis: building a framework. Cell. 2006; 127:679-95; Gao D, Nolan D J, Mellick A S, Bambino K, McDonnell K, Mittal V. Endothelial progenitor cells control the angiogenic switch in mouse lung metastasis. Science. 2008; 319:195-8; and Joyce J A, Pollard J W. Microenvironmental regulation of metastasis. Nat Rev Cancer. 2009; 9:239-52), are cultured in DMEM supplemented with 10% fetal bovine serum.

Tissue Microarrays and Immunohistochemistry

Archival specimens (radical prostatectomy specimens, or biopsies of metastases) are retrieved from files of Department of Pathology, The Gade Institute, Haukeland University Hospital. Formalin fixed prostatectomy specimens were paraffin embedded and studied by whole mount step sections at 5 mm intervals. Tissue microarrays (TMAs) were constructed selecting three tissue cores (0.6 mm in diameter) from the area of highest tumor grade in each case.

Thin paraffin sections (5 um) from the TMA paraffin block are dewaxed with xylene/ethanol before heat induced microwave epitope retrieval in citrate buffer (pH 6.0) for 20 minutes, and incubated with a CD36 antibody for 60 minutes at room temperature. Immunostaining is performed on the DAKO Autostainer with the EnVision chain polymer method (Dako Cytomation, Copenhagen, Denmark) as detection system. Antigen localization is achieved using the DAB diaminobenzidine peroxidase reaction, counterstained with hematoxylin.

Immunostaining is estimated semiquantitatively, and a staining index (SI) obtained as a product of staining intensity (0-3) and proportion of immunopositive tumor cells (<10%=1, 10-50%=2, >50%=3), is calculated. The staining index (range 0-9) is a categorical scale, where some variation within each category is expected.

Knockdown of CD36 in Tumor Cells

CD36 levels are decreased in cancer cell lines using retroviral or lentiviral vectors encoding miRNAs or shRNAs that target CD36. Knockdown efficiency is tested using qPCR analysis. Total RNA is extracted using the PicoPure RNA extraction kit (Arcturus) following the manufacturer's protocol. RNA is converted to cDNA using gScript™ cDNA supermix (Quanta biosciences). qPCR is performed with primers and iQ™ SYBER Green master mix (Biorad, Hercule, Calif.). A standard protocol of initial denaturing at 95° C. for 10 min, 40 cycles of 95° C. for 10 sec, 60° C. for 30 sec, and 72° C. for 30 sec, followed by final extension at 72° C. for 5 min and melt curve analysis is applied on a BioRad CFX96 Real Time System (BioRad) coupled with Bio-Rad-CFX Manager software. The relative abundance of each transcript compared with the control is calculated utilizing the delta-Ct method.

In Vitro Cell Proliferation Assays

Cell proliferation is measured using the MTT (3-{4,5-Dimethylthiazol-2-yl}-2,5-diphenyltetrazolium bromide, Sigma-Aldrich) assay. Cells are seeded in 50 uL growth medium in 96 well culture plates and allowed to attach overnight. 50 uL of growth medium plus two-fold concentrated treatment reagents were then added. After each treatment time point, 10 uL of 5% MTT solution (buffered in PBS) was added to each well. Plates were incubated for an additional 4 h at 37° C. to allow MTT to be metabolically converted into formazan crystals at cell mitochondria. The formazan crystals were finally solubilized by adding 100 ul of 10% Sodium Dodecyl Sulphate in 50% N—N-Dimethylformamide to each microplate well. Absorbances at 550 and 680 nm (corresponding to formazan salt and reference wavelengths, respectively) were measured using a colorimetry microplate reader. Wells containing only complete medium were used as controls. Each experiment was performed twice, using six replicates for each drug concentration.

Metastasis Assay, Bioluminescence Imaging and Analysis

For experimental metastasis, 7-week old C57BL/6 mice are injected via tail vein with $1 \times 10^5$ luciferase-labeled LLC cells. For orthotopic breast cancer cell injections, $5 \times 10^6$ MDA-MB-231 or its metastatic variant MDA-MB-LM2 cells, are injected into CB-17 SCID mice fat pads in a volume of 0.1 ml. Tumor growth and pulmonary metastases (following resection of primary tumor) were monitored by live animal bioluminescence imaging (Xenogen) once per week. For orthotopic prostate cancer cell injections, 2×106 viable LN4 or cells were injected into the prostate gland of mice.

For in vivo determination of the metastatic burden, mice were anaesthetized and injected intraperitoneally with 75 mg/kg of D-luciferin (100 uL of 30 mg/mL in PBS). Metastatic growth was monitored over time using bioluminescence imaging performed with mice in a supine position 5 min after D-luciferin injection with a Xenogen IVIS system coupled to Living Image acquisition and analysis software (Xenogen). For BLI plots, photon flux was calculated for each mouse by using the same circular region of interest encompassing the thorax of the mouse.

Psap Peptide Administration 8-week old mice are treated with a Psap peptide (such as DWLPK (SEQ ID NO: 2), DWLP (SEQ ID NO: 3), or a modified version thereof), diluted in PBS, at a dose of 30 mg/kg/day via intraperitoneal injection for up to two weeks.

Results

CD36 levels are measured in tissue samples from human subjects with cancer.

CD36 levels are knocked down in cancer cell lines and these cell lines with reduced CD36 are injected into mice. Mice are then administered a Psap peptide. Tumor growth and metastatic burden are monitored. It is expected that knockdown of CD36 in cancer cells will reduce the anticancer activity of a Psap peptide in vivo.

Example 3

Methods

Except were stated otherwise, the methods used in Example 3 are the same as the methods used in Examples 1 and 2. The cell lines tested for CD36 expression were pancreatic (AsPC1), ovarian (DF-14 and ID-8), breast (MDA-MB231 and LM2), prostate (PC3, PC3-M-LN4, LN-CAP, and LN-CAP-LN3), melanoma (B16-B16), and lung cancer (LLC) cell lines. All of these cell lines are known in the art and/or commercially available.

Ovarian cancer cells expressing CD36 were treated with either control or thrombospondin (Tsp-1, either 100 ng, 500 ng or 1000 ng) and the percent of viable cells was measured at 0 hours or 48 hours.

For the ovarian cancer mouse model, 1 million ovarian cancer cells expressing luciferase were injected intraperitoneally. Treatment was initiated 17 days later with cisplatin (4 mg/kg QOD), the psap peptide dWlP (SEQ ID NO: 47, 40 mg/kg QD), a combination of cisplatin and psap peptide, or PBS QD. Luciferase intensity was measured on several days beginning on about day 17 and measured over time.

For the pancreatic cancer mouse model, $1 \times 10^6$ AsPc1 human pancreatic cells were injected into the pancreas of SCID mice. Mice were treated either with a control or with the psap peptide dWlP (SEQ ID NO: 47, 20 mg/kg/day or 40/mg/kg/day). Treatment began on day 25 and continued daily for 21 days. The mice were then euthanized and the primary tumor mass was measured. The presence or absence of ascites was also measured.

For the melanoma mouse model, B16-B16 cells were injected into mice. Mice were treated with either psap peptide dWlP (SEQ ID NO: 47, 10 or 40 mg/kg) or control. The volume of the tumor was measured over time up until about 20-25 days post cell injection.

Results

Figure 5:
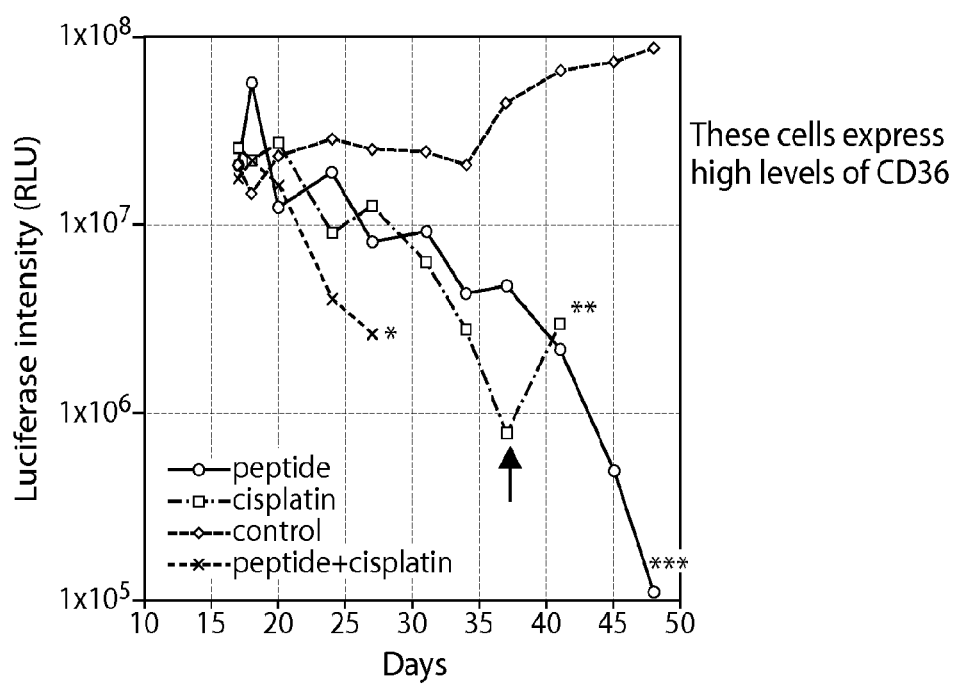
FIG. 5 is a graph showing that dWIP (SEQ ID NO: 47) peptide caused regression of cancer in a cancer model that expresses high levels of CD36.

Multiple cancer cell lines were tested for expression of CD36. It was found that CD36 protein was detectable in all cell lines tested, with particularly high levels of CD36 detectable in AsPC1, DF-14, MDA-MB231, and PC3 cell lines (FIG. 5).

Figure 6:
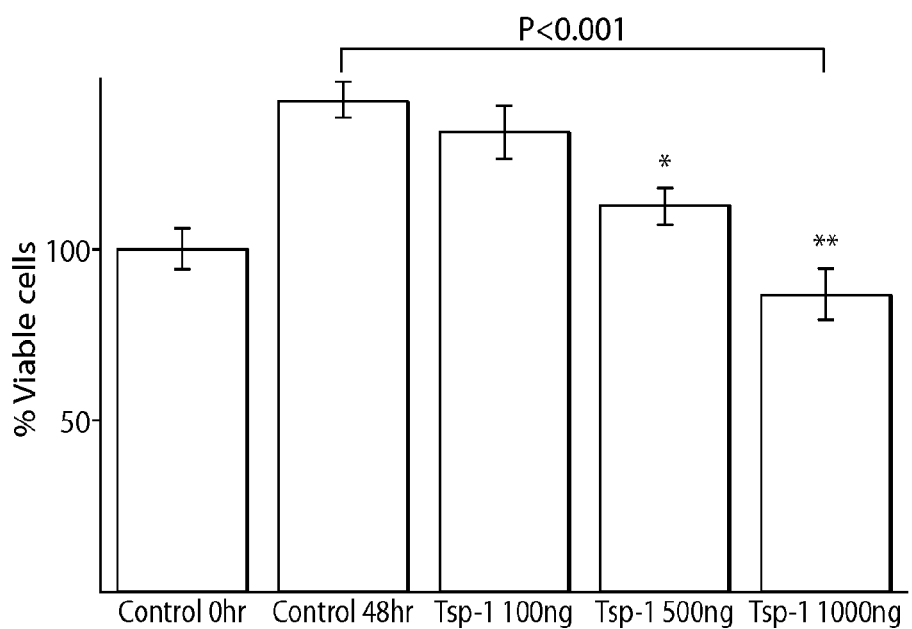
FIG. 6 is a graph showing that ovarian Cancer cells expressing CD36 are sensitive to Tsp-1 mediated cell killing.

It was shown that ovarian cells expressing CD36 were sensitive to Tsp-1 mediated cell killing in a dose-dependent manner (FIG. 6).

Figure 7:
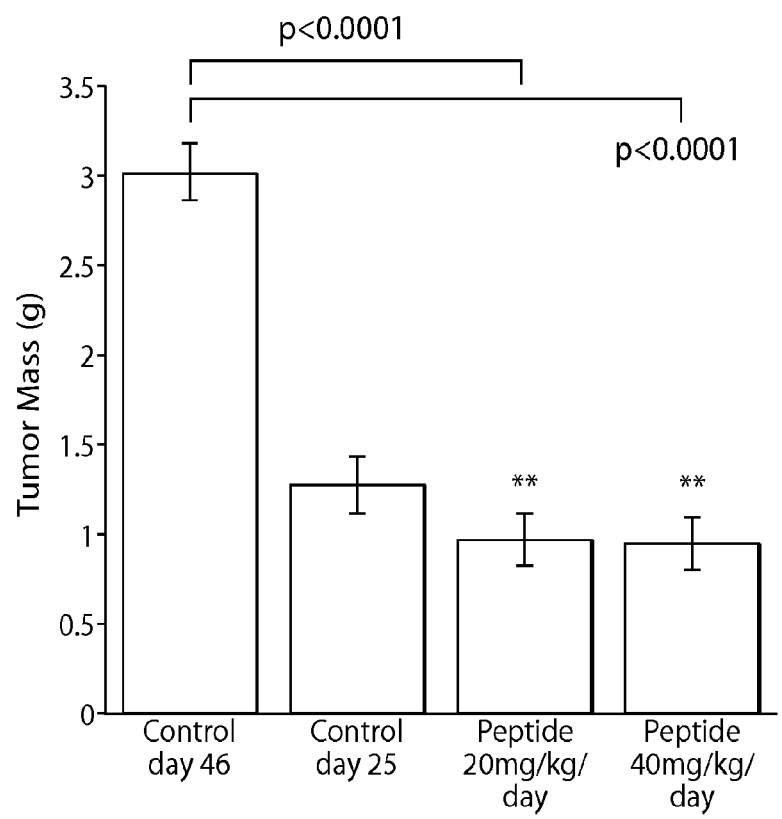
FIG. 7 is a graph showing the primary tumor mass of mice injected with AsPC pancreatic cancer cells that express high levels of CD36 and then treated with dWIP (SEQ ID NO: 47) peptide or control. The primary tumor mass was inhibited by peptide treatment.
Figure 8:
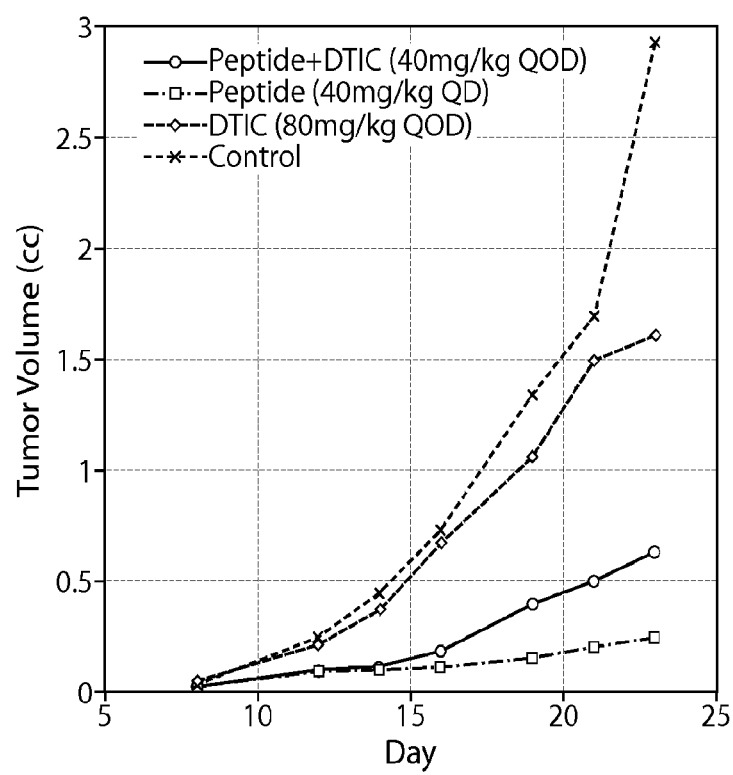
FIG. 8 is a graph showing that treatment of mice with B16-B16 melanoma tumors (which express low levels of CD36) with dWIP (SEQ ID NO: 47) peptide inhibited tumor growth but did not regress the tumor.

Two "high" CD36 cell lines (ovarian cancer cells and AsPC pancreatic cancer cells) and one "low" CD36 cell line (B16-B6 cancer cells) were injected into mice to study the effects of psap peptides on tumor growth and metastasis. It was found that the "high" CD36 cancer models regressed in response to psap peptide treatment (FIGS. 5 and 7). The ovarian cancer model also showed regression of metastatic disease (FIG. 5). The pancreatic cancer model also showed inhibition of metastasis because only 1 of 19 mice treated with a psap peptide form ascites, while 4 of 10 mice treated with the control formed ascites. In the "low" CD36 melanoma model, it was found that treatment with a psap peptide inhibited primary tumor growth but did not cause tumor regression (FIG. 8). These results show that "high" CD36 cancers are more likely to strongly respond to psap peptide treatment (e.g., regression of primary tumor and/or metastasis), while "low" CD36 cancers are more likely to have a weaker response (e.g., inhibition of primary tumor rather than regression).

Without further elaboration, it is believed that one skilled in the art can, based on the above description, utilize the present disclosure to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

The indefinite articles "a" and "an," as used herein in the specification and in the claims, unless clearly indicated to the contrary, should be understood to mean "at least one."

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method for treating cancer in a subject in need thereof, the method comprising: administering to the subject an effective amount of a prosaposin (Psap) peptide, wherein the cancer is characterized by an elevated level of CD36 as compared to a control level of CD36, and wherein the Psap peptide consists of a sequence selected from the group consisting of CDWLPK (SEQ ID NO: 1), DWLPK (SEQ ID NO: 2), and DWLP (SEQ ID NO: 3).

2. The method of claim 1, wherein the control level is a level of CD36 in a cell or tissue obtained from a healthy subject or a population of healthy subjects.

3. The method of claim 1, wherein the control level is a predetermined level.

4. The method of claim 1, wherein the level of CD36 is a CD36 protein level.

5. The method of claim 1, wherein the cancer is prostate cancer, breast cancer, ovarian cancer, lung cancer, leukemia, pancreatic cancer, glioblastoma multiforme, astrocytoma, or melanoma.

6. The method of claim 1, wherein the Psap peptide is a cyclic peptide.

7. The method of claim 1, wherein the control level is a level of CD36 from a non-cancerous cell or tissue obtained from the subject having the cancer.

8. The method of claim 1, wherein the Psap peptide comprises one or more modifications selected from the group consisting of acetylation, pegylation, and conjugation to a non-peptide polymer that enhances serum half-life of the peptide.

9. The method of claim 1, wherein the Psap peptide is a dimer, trimer, or multimer.

* * * * *

UNITED STATES PATENT AND TRADEMARK OFFICE
CERTIFICATE OF CORRECTION

| | |
|---|---|
| PATENT NO. | : 9,921,224 B2 |
| APPLICATION NO. | : 14/773596 |
| DATED | : March 20, 2018 |
| INVENTOR(S) | : Randolph S. Watnick |

It is certified that error appears in the above-identified patent and that said Letters Patent is hereby corrected as shown below:

In the Specification

Column 1, Lines 22 to 24, "R01CA135417 awarded by the National Cancer Institute" should read -- Grant Number CA135417, awarded by the National Institutes of Health --.

Signed and Sealed this
Fifth Day of September, 2023

Katherine Kelly Vidal
*Director of the United States Patent and Trademark Office*

SEQUENCE LISTING

<160> NUMBER OF SEQ ID NOS: 48

<210> SEQ ID NO 1
<211> LENGTH: 6
<212> TYPE: PRT
<213> ORGANISM: Artificial sequence
<220> FEATURE:
<223> OTHER INFORMATION: Psap peptide

<400> SEQUENCE: 1

Cys Asp Trp Leu Pro Lys
1               5

<210> SEQ ID NO 2
<211> LENGTH: 5
<212> TYPE: PRT
<213> ORGANISM: Artificial sequence
<220> FEATURE:
<223> OTHER INFORMATION: Psap peptide

<400> SEQUENCE: 2

Asp Trp Leu Pro Lys
1               5

<210> SEQ ID NO 3
<211> LENGTH: 4
<212> TYPE: PRT
<213> ORGANISM: Artificial sequence
<220> FEATURE:
<223> OTHER INFORMATION: Psap peptide

<400> SEQUENCE: 3

Asp Trp Leu Pro
1

<210> SEQ ID NO 4
<211> LENGTH: 4727
<212> TYPE: DNA
<213> ORGANISM: H. sapiens

<400> SEQUENCE: 4
ctttcaattc tctctggcaac aaaccacaca ctgggatctg acactgtaga gtgctttctc      60
ttctcttttt ttgggggggg gaggggggtgt ggttgcatat ttaaactctc acgcatttat     120
gtactgagga ctgcagtgta ggactttcct gcagaatacc atttgatcct attaagaatt     180
gtccaaatgt tggagcattt gattgaaaaa tccttcttag ccattttaaa gatagctttc     240
caatgattag acgaattgat tctttctgtg actcatcagt tcatttcctg taaaattcat     300

```
gtcttgctgt tgatttgtga ataagaacca gagcttgtag aaaccacttt aatcatatcc      360
aggagtttgc aagaaacagg tgcttaacac taattcacct cctgaacaag aaaaatgggc      420
tgtgaccgga actgtgggct catcgctggg gctgtcattg gtgctgtcct ggctgtgttt      480
ggaggtattc taatgccagt tggagacctg cttatccaga agacaattaa aaagcaagtt      540
gtcctcgaag aaggtacaat tgcttttaaa aattgggtta aacaggcac agaagtttac       600 agacagtttt ggatctttga tgtgcaaaat ccacaggaag tgatgatgaa cagcagcaac      660
attcaagtta agcaaagagg tccttatacg tacagagttc gttttctagc caaggaaaat      720
gtaacccagg acgctgagga caacacagtc tctttcctgc agcccaatgg tgccatcttc      780
gaaccttcac tatcagttgg aacagaggct gacaacttca cagttctcaa tctggctgtg      840
gcagctgcat cccatatcta tcaaaatcaa tttgttcaaa tgatcctcaa ttcacttatt      900
aacaagtcaa aatcttctat gttccaagtc agaactttga gagaactgtt atggggctat      960
agggatccat ttttgagttt ggttccgtac cctgttacta ccacagttgg tctgttttat     1020
ccttacaaca atactgcaga tggagtttat aaagttttca tggaaaaga taacataagt      1080 aaagttgcca taatcgacac atataaaggt aaaaggaatc tgtcctattg ggaaagtcac     1140
tgcgacatga ttaatggtac agatgcagcc tcatttccac cttttgttga gaaaagccag     1200
gtattgcagt tcttttcttc tgatatttgc aggtcaatct atgctgtatt tgaatccgac     1260
gttaatctga aggaatcccc tgtgtataga tttgttcttc catccaaggc ctttgcctct     1320
ccagttgaaa acccagacaa ctattgtttc tgcacagaaa aaattatctc aaaaaattgt     1380
acatcatatg gtgtgctaga catcagcaaa tgcaagaag ggagacctgt gtacatttca     1440
cttcctcatt ttctgtatgc aagtcctgat gtttcagaac ctattgatgg attaaaccca     1500
aatgaagaag aacataggac atacttggat attgaaccta taactggatt cactttacaa     1560
tttgcaaaac ggctgcaggt caacctattg gtcaagccat cagaaaaaat tcaagtatta     1620
aagaatctga gaggaactaa tattgtgcct attctttggc ttaatgagac tgggaccatt     1680
ggtgatgaga aggcaaacat gttcagaagt caagtaactg gaaaaataaa cctccttggc     1740
ctgatagaaa tgatcttact cagtgttggt gtggtgatgt tgttgctttt tatgatttca     1800
tattgtgcat gcagatcgaa aacaataaaa taaacctggc tcaagcacaa accaatttgt     1860
gttgttctga ttcaataatt ggtttctggg tggccaattc agaagaagag tgtacatgct     1920
caacaaatcc taggccctgc attcctgtca tcctcatccg ggggaaacac catcatccca     1980
gtagctgccc tattcaactg caacagtctc caggaccatc agtatactgc atttcatgtg     2040
caccaaatat tttgaaagac atttataaat aattggctta tgactcatat ttctctatga     2100
ataccttcat acagcaggta taactctttt ctttatgggc ttaaatattt tgtcactgat     2160
cctgcaaatg gacatcattt tagcacacta gcggtttata ttttaaggac cttcattctc     2220
tgttctgcac ctcttctgga aattgagtaa attttgcttt tttttttta ctcagttgca      2280 acttacgctt ggcatcttca gaatgctttt ctagcattaa gagatgtaaa tgataaagga     2340
attattgtat gaaatattac aaagcgtaga ctatgcattg ttattcatta taatattttt     2400
tgctgtcata atcgcctcat aaagacaggt ttcaaccatt aaaatatgtt cttccttaaa     2460
ttcctgtgct ttttctagtt cctcttgtgt cataaaatgt ttatcctaat tttctctctg     2520
aagtatattt tatctgaatc cacatttctt tataaatcca tagtccttgc tgaaatatgc     2580
tttctaaatt tctaccactt tgttctaggc taattttta agctaattgg atgaagaaca      2640
```

```
aaaagacatt tggtttcatc cttttacagca gtaggacaat tgcaaaggtt tttccttttt    2700
cataaggaga cacattaata ggtaactctg tttcttgagc aggggttcac ttattctgag    2760
agcattagtt ctcctaaaaa gctccagcat agaaagggaa gataaaccaa attctagctt    2820
gtgttttacc cacagaagga tacaggacaa aggaatagta actggcctgt ttggatacta    2880
aaatcgaaaa taacttttag cctcctcctt atgatagccg ccagagtaaa tgttgagcat    2940
tactacagaa aagccacaaa ccaagaatct acctgtttgg aaagatcttt tgcatctctg    3000
aaggtgctta aagcatactt agtgcctttc cttttaactg ggaagataaa agaagtatct    3060
gtccaagata ttaatatgta agataacatt gtagacatgt tcttctgata atacaaggtt    3120
tattctattt gcattaggat atttgtggac atgtccatct aatataaagg aaagtttttt    3180
aatcattgag gcatgtaggg ctgagttata taatgtagaa acttctaaag ataattggat    3240
gagaatatac atattgacct gtatattatg actaatcatg actcagatct taatacaggg    3300
atgatctcat agcatttaga tatcagaaaa ggttttgacc tatatgtctt taatattgtt    3360
tgaatacatg tataatcttt atcattcctc agtgtttcat ttctcaaatt ctgtaaaagg    3420
aatataagag gaaagacaat tcatatacaa agacaacgag attaaaaata tgcagtagga    3480
aaaataatta cttaagggga gattttttt acatgaaatc tgggctttgg atgtgtgtgt    3540
gtgtgtgtgt gtgtgtgtgt gtgcacatat gcactgtggt gggagtgggg caacttgggg    3600
aatatgttac atgtgtgact ttgttttgcc ctggcgaagt taatgttgtt cagaaagggt    3660
aaatgtttgg acacttgcaa ttgctcatgg atgaatttat atgttttagt catagaaaaa    3720
ttgtaccctt tgatagaagc acattttctt tccaaagctg gttattaacc acagaattat    3780
agcaggtatt cataacttaa gtttgaaaat caatagcgtc tgcaaatgga ttaacagatt    3840
agagaatcaa cagcatcgga aaataggtta atgcatattg cttctaacaa gtgcatgaag    3900
aaatagaaga agctatgtag ctttcagttc tgacagaaaa gggtgaagga gggtatcatt    3960
tcaagaaaaa aaatagctat cacgcaatgg ttatctctga aaatatttgt attaagatgt    4020
gtatacatgg ccaggcatgg tggctcatgc ctgtaatccc agcactttgg gaggcaggtg    4080
gatcacgagg tcaggagatc aagaccatcc tggccaacat ggtgaaacct catctctact    4140
aaaaatacaa aaatgagcgg ggtgtggtgg cccatgcctg tagtcccagc tgctcgggag    4200
actgaatctc ttgagcctgg gaagcagagg ttgcagtgaa ctgagatcgc gtcactgcac    4260
tccagcctgg tgacagagcg agattccatc tcaaaaaaaa aaaacagtat gcacgtacaa    4320
atttcttaac ctgttatcaa tgtctgagct acataattat cttttctagtt ggagtttgtt    4380 ttaggtgtgt accaactgac atttcagttt ttctgtttga agtccaatgt attagtgact    4440
ctgtggctgc tctcttcacc tgcccttgt ggcctgtcta caattctaaa tggattttga    4500
actcaatgtc gtcgcttctg gtttcctgca tataccaata gcattaccta tgactttttt    4560
tttcctgagc tattttcact gagctgagct aatgaactaa aactgagtta tgtttaatat    4620
ttgtatcaaa tacataaaag gaatactgct ttttcctttt gtggctcaaa ggtagctgca    4680
ttttaaaata tttgtgaaaa taaaaacttt tgttattaga aaaatga                  4727
```

<210> SEQ ID NO 5
<211> LENGTH: 2069
<212> TYPE: DNA
<213> ORGANISM: H. sapiens

<400> SEQUENCE: 5

```
gaggatgtca atggctttca gatgtcagga taaccttaag gatagatgaa gggttgagag      60
```

```
cctgtgcctc atttctgagt tctcagctgc tatgccgtgg aaatcctgtt tactttctgc      120
atctgctcct gcaagactct ggagccagtc ttgaggtcct acatctccga aagcaagctc      180
ttctagaagt tgatagcttt ccaatgatta gacgaattga ttctttctgt gactcatcag      240
ttcatttcct gtaaaattca tgtcttgctg ttgatttgtg aataagaacc agagcttgta      300
gaaaccactt taatcatatc caggagtttg caagaaacag gtgcttaaca ctaattcacc      360
tcctgaacaa gaaaaatggg ctgtgaccgg aactgtgggc tcatcgctgg ggctgtcatt      420
ggtgctgtcc tggctgtgtt tggaggtatt ctaatgccag ttggagacct gcttatccag      480
aagacaatta aaaagcaagt tgtcctcgaa gaaggtacaa ttgctttaa aaattgggtt       540 aaaacaggca cagaagttta cagacagttt tggatctttg atgtgcaaaa tccacaggaa      600
gtgatgatga acagcagcaa cattcaagtt aagcaaagag gtccttatac gtacagagtt      660
cgttttctag ccaaggaaaa tgtaacccag gacgctgagg acaacacagt ctctttcctg      720
cagcccaatg gtgccatctt cgaaccttca ctatcagttg gaacagaggc tgacaacttc      780
acagttctca atctggctgt ggcagctgca tcccatatct atcaaaatca atttgttcaa      840
atgatcctca attcacttat taacaagtca aaatcttcta tgttccaagt cagaactttg      900
agagaactgt tatggggcta tagggatcca ttttgagtt tggttccgta ccctgttact       960
accacagttg gtctgtttta tccttacaac aatactgcag atggagttta taaagttttc     1020
aatggaaaag ataacataag taaagttgcc ataatcgaca catataaagg taaaaggaat     1080
ctgtcctatt gggaaagtca ctgcgacatg attaatggta cagatgcagc ctcatttcca     1140
ccttttgttg agaaaagcca ggtattgcag ttcttttctt ctgatatttg caggtcaatc     1200
tatgctgtat ttgaatccga cgttaatctg aaaggaatcc ctgtgtatag atttgttctt     1260
ccatccaagg cctttgcctc tccagttgaa aacccagaca actattgttt ctgcacagaa     1320
aaaattatct caaaaaattg tacatcatat ggtgtgctag acatcagcaa atgcaaagaa     1380
gggagacctg tgtacatttc acttcctcat tttctgtatg caagtcctga tgtttcagaa     1440
cctattgatg gattaaaccc aaatgaagaa gaacatagga catacttgga tattgaacct     1500
ataactggat tcactttaca atttgcaaaa cggctgcagg tcaacctatt ggtcaagcca     1560
tcagaaaaaa ttcaagtatt aaagaatctg aagaggaact atattgtgcc tattctttgg     1620
cttaatgaga ctgggaccat tggtgatgag aaggcaaaca tgttcagaag tcaagtaact     1680
ggaaaaataa acctccttgg cctgatagaa atgatcttac tcagtgttgg tgtggtgatg     1740
tttgttgctt ttatgatttc atattgtgca tgcagatcga aaacaataaa ataagtaagt     1800
atgtaccaaa aaatattgct tcaataatat tagcttatat attacttgtt ttcactttat     1860
caaagagaag ttcatatatta ggccatatat atttctagac atgtctagcc actgatcatt    1920
tttaaatata ggtaaataaa cctataaata ttatcacgca gatcactaaa gtatatcttt     1980
aattctggga gaaatgagat aaaagatgta cttgtgacca ttgtaacaat agcacaaata     2040
aagcacttgt gccaaagttg tccaaaaaa                                        2069
```

<210> SEQ ID NO 6
<211> LENGTH: 2108
<212> TYPE: DNA
<213> ORGANISM: H. sapiens

<400> SEQUENCE: 6

```
ctttcaattc ctctggcaac aaaccacaca ctgggatctg acactgtaga gtgctttctc       60
```

```
ttctcttttt ttggggggggg gagggggtgt ggttgcatat ttaaactctc acgcatttat      120
gtactgagga ctgcagtgta ggactttcct gcagaatacc atttgatcct attaagaatt      180
gtccaaatgt tggagcattt gattgaaaaa tccttcttag ccatttaaa gatagctttc       240
caatgattag acgaattgat tctttctgtg actcatcagt tcatttcctg taaaattcat      300
gtcttgctgt tgatttgtga ataagaacca gagcttgtag aaaccacttt aatcatatcc      360
aggagtttgc aagaaacagg tgcttaacac taattcacct cctgaacaag aaaaatgggc      420
tgtgaccgga actgtgggct catcgctggg gctgtcattg gtgctgtcct ggctgtgttt      480
ggaggtattc taatgccagt tggagacctg cttatccaga agacaattaa aaagcaagtt      540
gtcctcgaag aaggtacaat tgcttttaaa aattgggtta aaacaggcac agaagtttac      600
agacagtttt ggatctttga tgtgcaaaat ccacaggaag tgatgatgaa cagcagcaac      660
attcaagtta agcaaagagg tccttatacg tacagagttc gttttctagc caaggaaaat      720
gtaacccagg acgctgagga caacacagtc tctttcctgc agcccaatgg tgccatcttc      780
gaaccttcac tatcagttgg aacagaggct gacaacttca cagttctcaa tctggctgtg      840
gcagctgcat cccatatcta tcaaaatcaa tttgttcaaa tgatcctcaa ttcacttatt      900
aacaagtcaa atcttctat gttccaagtc agaactttga gagaactgtt atggggctat      960
agggatccat ttttgagttt ggttccgtac cctgttacta ccacagttgg tctgttttat      1020
ccttacaaca atactgcaga tggagtttat aaagttttca tggaaaaga taacataagt      1080
aaagttgcca taatcgacac atataaaggt aaaaggaatc tgtcctattg ggaaagtcac      1140
tgcgacatga ttaatggtac agatgcagcc tcatttccac cttttgttga gaaaagccag      1200
gtattgcagt tcttttcttc tgatatttgc aggtcaatct atgctgtatt tgaatccgac      1260
gttaatctga aaggaatccc tgtgtataga tttgttcttc catccaaggc ctttgcctct      1320
ccagttgaaa acccagacaa ctattgtttc tgcacagaaa aaattatctc aaaaaattgt      1380
acatcatatg gtgtgctaga catcagcaaa tgcaaagaag ggagacctgt gtacatttca      1440
cttcctcatt ttctgtatgc aagtcctgat gtttcagaac ctattgatgg attaaaccca      1500
aatgaagaag aacataggac atacttggat attgaaccta aactggatt cactttacaa      1560
tttgcaaaac ggctgcaggt caacctattg gtcaagccat cagaaaaat tcaagtatta      1620
aagaatctga gaggaacta tattgtgcct attctttggc ttaatgagac tgggaccatt      1680
ggtgatgaga aggcaaacat gttcagaagt caagtaactg gaaaaataaa cctccttggc      1740
ctgatagaaa tgatcttact cagtgttggt gtggtgatgt tgttgctttt tatgatttca      1800
tattgtgcat gcagatcgaa aacaataaaa taagtaagta tgtaccaaaa atatgttctt      1860
caataatatt agcttatata ttacttgttt tcactttatc aaagagaagt tacatattag      1920
gccatatata tttctagaca tgtctagcca ctgatcattt ttaaatatag gtaaataaac      1980
ctataaatat tatcacgcag atcactaaag tatatcttta attctgggag aaatgagata      2040
aaagatgtac ttgtgaccat tgtaacaata gcacaaataa agcacttgtg ccaaagttgt      2100
ccaaaaaa                                                               2108
```

<210> SEQ ID NO 7
<211> LENGTH: 1814
<212> TYPE: DNA
<213> ORGANISM: H. sapiens

<400> SEQUENCE: 7

```
aagttgctga gacaagggaa gagagatgag gaaccagagc ttgtagaaac cactttaatc       60
```

```
atatccagga gtttgcaaga aacaggtgct taacactaat tcacctcctg aacaagaaaa    120
atgggctgtg accggaactg tgggctcatc gctggggctg tcattggtgc tgtcctggct    180
gtgtttggag gtattctaat gccagttgga gacctgctta tccagaagac aattaaaaag    240
caagttgtcc tcgaagaagg tacaattgct tttaaaaatt gggttaaaac aggcacagaa    300
gtttacagac agttttggat ctttgatgtg caaaatccac aggaagtgat gatgaacagc    360
agcaacattc aagttaagca aagaggtcct tatacgtaca gagttcgttt tctagccaag    420
gaaaatgtaa cccaggacgc tgaggacaac acagtctctt tcctgcagcc caatggtgcc    480
atcttcgaac cttcactatc agttggaaca gaggctgaca acttcacagt tctcaatctg    540
gctgtggcag ctgcatccca tatctatcaa aatcaatttg ttcaaatgat cctcaattca    600
cttattaaca agtcaaaatc ttctatgttc caagtcagaa ctttgagaga actgttatgg    660
ggctataggg atccattttt gagtttggtt ccgtaccctg ttactaccac agttggtctg    720
ttttatcctt acaacaatac tgcagatgga gtttataaag ttttcaatgg aaaagataac    780
ataagtaaag ttgccataat cgacacatat aaaggtaaaa ggaatctgtc ctattgggaa    840
agtcactgcg acatgattaa tggtacagat gcagcctcat ttccaccttt tgttgagaaa    900
agccaggtat tgcagttctt ttcttctgat atttgcaggt caatctatgc tgtatttgaa    960
tccgacgtta atctgaaagg aatccctgtg tatagatttg ttcttccatc caaggccttt   1020
gcctctccag ttgaaaaccc agacaactat tgtttctgca cagaaaaaat tatctcaaaa   1080
aattgtacat catatggtgt gctagacatc agcaaatgca aagaagggag acctgtgtac   1140
atttcacttc ctcattttct gtatgcaagt cctgatgttt cagaacctat tgatggatta   1200
aacccaaatg aagaagaaca taggacatac ttggatattg aacctataac tggattcact   1260
ttacaatttg caaaacggct gcaggtcaac ctattggtca agccatcaga aaaaattcaa   1320
gtattaaaga atctgaagag gaactatatt gtgcctattc tttggcttaa tgagactggg   1380
accattggtg atgagaaggc aaacatgttc agaagtcaag taactggaaa aataaacctc   1440
cttggcctga tagaaatgat cttactcagt gttggtgtgg tgatgtttgt tgcttttatg   1500
atttcatatt gtgcatgcag atcgaaaaca ataaaataag taagtatgta ccaaaaaata   1560
ttgcttcaat aatattagct tatatattac ttgttttcac tttatcaaag agaagttaca   1620
tattaggcca tatatatttc tagacatgtc tagccactga tcatttttaa atataggtaa   1680
ataaacctat aaatattatc acgcagatca ctaaagtata tctttaattc tgggagaaat   1740
gagataaaag atgtacttgt gaccattgta acaatagcac aaataaagca cttgtgccaa   1800
agttgtccaa aaaa                                                     1814
```

<210> SEQ ID NO 8
<211> LENGTH: 1989
<212> TYPE: DNA
<213> ORGANISM: H. sapiens

<400> SEQUENCE: 8

```
atgacattat tagttctgcc actggtaggc attagaagca agaaaaggga gacggaccga     60
ggaagccact ttggtgaaac aaaaagaaaa gcatttgttt atttagaacg ggcaaaatga    120
tacgtttcag tgggtgtttt ctttgtactt tgatcttttt gtactgatat ttaagcttct    180
gttttatgat ctctttctaa tgatagaacc agagcttgta gaaaccactt taatcatatc    240
caggagtttg caagaaacag gtgcttaaca ctaattcacc tcctgaacaa gaaaaatggg    300
```

```
ctgtgaccgg aactgtgggc tcatcgctgg ggctgtcatt ggtgctgtcc tggctgtgtt      360
tggaggtatt ctaatgccag ttggagacct gcttatccag aagacaatta aaaagcaagt      420
tgtcctcgaa gaaggtacaa ttgcttttaa aaattgggtt aaaacaggca cagaagttta      480
cagacagttt tggatctttg atgtgcaaaa tccacaggaa gtgatgatga acagcagcaa      540
cattcaagtt aagcaaagag gtccttatac gtacagagtt cgttttctag ccaaggaaaa      600
tgtaacccag gacgctgagg acaacacagt ctctttcctg cagcccaatg gtgccatctt      660
cgaaccttca ctatcagttg aacagaggc tgacaacttc acagttctca atctggctgt      720
ggcagctgca tcccatatct atcaaaatca atttgttcaa atgatcctca attcacttat      780
taacaagtca aaatcttcta tgttccaagt cagaactttg agagaactgt tatggggcta      840
tagggatcca ttttttgagtt tggttccgta ccctgttact accacagttg gtctgtttta      900
tccttacaac aatactgcag atggagttta taaagttttc aatggaaaag ataacataag      960
taaagttgcc ataatcgaca catataaagg taaaaggaat ctgtcctatt gggaaagtca     1020
ctgcgacatg attaatggta cagatgcagc ctcatttcca ccttttgttg agaaaagcca     1080
ggtattgcag ttcttttctt ctgatatttg caggtcaatc tatgctgtat ttgaatccga     1140
cgttaatctg aaaggaatcc ctgtgtatag atttgttctt ccatccaagg cctttgcctc     1200
tccagttgaa acccagaca actattgttt ctgcacagaa aaaattatct caaaaaattg     1260
tacatcatat ggtgtgctag acatcagcaa atgcaaagaa gggagacctg tgtacatttc     1320
acttcctcat tttctgtatg caagtcctga tgtttcagaa cctattgatg gattaaaccc     1380 aaaatgaagaa gaacatagga catacttgga tattgaacct ataactggat tcactttaca     1440
atttgcaaaa cggctgcagg tcaacctatt ggtcaagcca tcagaaaaaa ttcaagtatt     1500
aaagaatctg aagaggaact atattgtgcc tattctttgg cttaatgaga ctgggaccat     1560
tggtgatgag aaggcaaaca tgttcagaag tcaagtaact ggaaaaataa acctccttgg     1620
cctgatagaa atgatcttac tcagtgttgg tgtggtgatg tttgttgctt ttatgatttc     1680
atattgtgca tgcagatcga aaacaataaa ataagtaagt atgtaccaaa aatattgct     1740 tcaataatat tagcttatat attacttgtt ttcactttat caaagagaag ttacatatta     1800
ggccatatat atttctagac atgtctagcc actgatcatt tttaaatata ggtaaataaa     1860
cctataaata ttatcacgca gatcactaaa gtatatcttt aattctggga gaatgagat     1920 aaaagatgta cttgtgacca ttgtaacaat agcacaaata aagcacttgt gccaaagttg     1980
tccaaaaaa                                                            1989
```

<210> SEQ ID NO 9
<211> LENGTH: 472
<212> TYPE: PRT
<213> ORGANISM: H. sapiens

<400> SEQUENCE: 9

```
Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
            20                  25                  30

Leu Ile Gln Lys Thr Ile Lys Lys Gln Val Val Leu Glu Glu Gly Thr
        35                  40                  45

Ile Ala Phe Lys Asn Trp Val Lys Thr Gly Thr Glu Val Tyr Arg Gln
    50                  55                  60

Phe Trp Ile Phe Asp Val Gln Asn Pro Gln Glu Val Met Met Asn Ser
```

```
            65                  70                  75                  80
        Ser Asn Ile Gln Val Lys Gln Arg Gly Pro Tyr Thr Tyr Arg Val Arg
                            85                  90                  95

Phe Leu Ala Lys Glu Asn Val Thr Gln Asp Ala Glu Asp Asn Thr Val
                        100                 105                 110

Ser Phe Leu Gln Pro Asn Gly Ala Ile Phe Glu Pro Ser Leu Ser Val
                    115                 120                 125

Gly Thr Glu Ala Asp Asn Phe Thr Val Leu Asn Leu Ala Val Ala Ala
                130                 135                 140

Ala Ser His Ile Tyr Gln Asn Gln Phe Val Gln Met Ile Leu Asn Ser
        145                 150                 155                 160

Leu Ile Asn Lys Ser Lys Ser Met Phe Gln Val Arg Thr Leu Arg
                        165                 170                 175

Glu Leu Leu Trp Gly Tyr Arg Asp Pro Phe Leu Ser Leu Val Pro Tyr
                    180                 185                 190

Pro Val Thr Thr Thr Val Gly Leu Phe Tyr Pro Tyr Asn Asn Thr Ala
                195                 200                 205

Asp Gly Val Tyr Lys Val Phe Asn Gly Lys Asp Asn Ile Ser Lys Val
            210                 215                 220

Ala Ile Ile Asp Thr Tyr Lys Gly Lys Arg Asn Leu Ser Tyr Trp Glu
        225                 230                 235                 240

Ser His Cys Asp Met Ile Asn Gly Thr Asp Ala Ala Ser Phe Pro Pro
                        245                 250                 255

Phe Val Glu Lys Ser Gln Val Leu Gln Phe Phe Ser Ser Asp Ile Cys
                    260                 265                 270

Arg Ser Ile Tyr Ala Val Phe Glu Ser Asp Val Asn Leu Lys Gly Ile
                275                 280                 285

Pro Val Tyr Arg Phe Val Leu Pro Ser Lys Ala Phe Ala Ser Pro Val
            290                 295                 300

Glu Asn Pro Asp Asn Tyr Cys Phe Cys Thr Glu Lys Ile Ile Ser Lys
        305                 310                 315                 320

Asn Cys Thr Ser Tyr Gly Val Leu Asp Ile Ser Lys Cys Lys Glu Gly
                        325                 330                 335

Arg Pro Val Tyr Ile Ser Leu Pro His Phe Leu Tyr Ala Ser Pro Asp
                    340                 345                 350

Val Ser Glu Pro Ile Asp Gly Leu Asn Pro Asn Glu Glu His Arg
                355                 360                 365

Thr Tyr Leu Asp Ile Glu Pro Ile Thr Gly Phe Thr Leu Gln Phe Ala
            370                 375                 380

Lys Arg Leu Gln Val Asn Leu Leu Val Lys Pro Ser Glu Lys Ile Gln
        385                 390                 395                 400

Val Leu Lys Asn Leu Lys Arg Asn Tyr Ile Val Pro Ile Leu Trp Leu
                        405                 410                 415

Asn Glu Thr Gly Thr Ile Gly Asp Glu Lys Ala Asn Met Phe Arg Ser
                    420                 425                 430

Gln Val Thr Gly Lys Ile Asn Leu Leu Gly Leu Ile Glu Met Ile Leu
                435                 440                 445

Leu Ser Val Gly Val Val Met Phe Val Ala Phe Met Ile Ser Tyr Cys
            450                 455                 460

Ala Cys Arg Ser Lys Thr Ile Lys
        465                 470

<210> SEQ ID NO 10
```

<211> LENGTH: 524
<212> TYPE: PRT
<213> ORGANISM: H. sapiens

<400> SEQUENCE: 10

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val

-continued

```
             385                 390                 395                 400
    Thr Gln Pro Lys Asp Gly Gly Phe Cys Glu Val Cys Lys Lys Leu Val
                    405                 410                 415

Gly Tyr Leu Asp Arg Asn Leu Glu Lys Asn Ser Thr Lys Gln Glu Ile
                    420                 425                 430

Leu Ala Ala Leu Glu Lys Gly Cys Ser Phe Leu Pro Asp Pro Tyr Gln
                    435                 440                 445

Lys Gln Cys Asp Gln Phe Val Ala Glu Tyr Glu Pro Val Leu Ile Glu
                    450                 455                 460

Ile Leu Val Glu Val Met Asp Pro Ser Phe Val Cys Leu Lys Ile Gly
    465                 470                 475                 480

Ala Cys Pro Ser Ala His Lys Pro Leu Leu Gly Thr Glu Lys Cys Ile
                    485                 490                 495

Trp Gly Pro Ser Tyr Trp Cys Gln Asn Thr Glu Thr Ala Ala Gln Cys
                    500                 505                 510

Asn Ala Val Glu His Cys Lys Arg His Val Trp Asn
                    515                 520

<210> SEQ ID NO 11
<211> LENGTH: 527
<212> TYPE: PRT
<213> ORGANISM: H. sapiens

<400> SEQUENCE: 11

Met Tyr Ala Leu Phe Leu Leu Ala Ser Leu Leu Gly Ala Ala Leu Ala
    1               5                   10                  15

Gly Pro Val Leu Gly Leu Lys Glu Cys Thr Arg Gly Ser Ala Val Trp
                    20                  25                  30

Cys Gln Asn Val Lys Thr Ala Ser Asp Cys Gly Ala Val Lys His Cys
                    35                  40                  45

Leu Gln Thr Val Trp Asn Lys Pro Thr Val Lys Ser Leu Pro Cys Asp
                    50                  55                  60

Ile Cys Lys Asp Val Val Thr Ala Ala Gly Asp Met Leu Lys Asp Asn
    65                  70                  75                  80

Ala Thr Glu Glu Glu Ile Leu Val Tyr Leu Glu Lys Thr Cys Asp Trp
                    85                  90                  95

Leu Pro Lys Pro Asn Met Ser Ala Ser Cys Lys Glu Ile Val Asp Ser
                    100                 105                 110

Tyr Leu Pro Val Ile Leu Asp Ile Ile Lys Gly Glu Met Ser Arg Pro
                    115                 120                 125

Gly Glu Val Cys Ser Ala Leu Asn Leu Cys Glu Ser Leu Gln Lys His
                    130                 135                 140

Leu Ala Glu Leu Asn His Gln Lys Gln Leu Glu Ser Asn Lys Ile Pro
    145                 150                 155                 160

Glu Leu Asp Met Thr Glu Val Val Ala Pro Phe Met Ala Asn Ile Pro
                    165                 170                 175

Leu Leu Leu Tyr Pro Gln Asp Gly Pro Arg Ser Lys Pro Gln Pro Lys
                    180                 185                 190

Asp Asn Gly Asp Val Cys Gln Asp Cys Ile Gln Met Val Thr Asp Ile
                    195                 200                 205

Gln Thr Ala Val Arg Thr Asn Ser Thr Phe Val Gln Ala Leu Val Glu
                    210                 215                 220

His Val Lys Glu Glu Cys Asp Arg Leu Gly Pro Gly Met Ala Asp Ile
    225                 230                 235                 240
```

```
Cys Lys Asn Tyr Ile Ser Gln Tyr Ser Glu Ile Ala Ile Gln Met Met
                245                 250                 255

Met His Met Gln Asp Gln Gln Pro Lys Glu Ile Cys Ala Leu Val Gly
            260                 265                 270

Phe Cys Asp Glu Val Lys Glu Met Pro Met Gln Thr Leu Val Pro Ala
        275                 280                 285

Lys Val Ala Ser Lys Asn Val Ile Pro Ala Leu Glu Leu Val Glu Pro
    290                 295                 300

Ile Lys Lys His Glu Val Pro Ala Lys Ser Asp Val Tyr Cys Glu Val
305                 310                 315                 320

Cys Glu Phe Leu Val Lys Glu Val Thr Lys Leu Ile Asp Asn Asn Lys
                325                 330                 335

Thr Glu Lys Glu Ile Leu Asp Ala Phe Asp Lys Met Cys Ser Lys Leu
            340                 345                 350

Pro Lys Ser Leu Ser Glu Glu Cys Gln Glu Val Val Asp Thr Tyr Gly
        355                 360                 365

Ser Ser Ile Leu Ser Ile Leu Leu Glu Glu Val Ser Pro Glu Leu Val
    370                 375                 380

Cys Ser Met Leu His Leu Cys Ser Gly Thr Arg Leu Pro Ala Leu Thr
385                 390                 395                 400

Val His Val Thr Gln Pro Lys Asp Gly Gly Phe Cys Glu Val Cys Lys
                405                 410                 415

Lys Leu Val Gly Tyr Leu Asp Arg Asn Leu Glu Lys Asn Ser Thr Lys
            420                 425                 430

Gln Glu Ile Leu Ala Ala Leu Glu Lys Gly Cys Ser Phe Leu Pro Asp
        435                 440                 445

Pro Tyr Gln Lys Gln Cys Asp Gln Phe Val Ala Glu Tyr Glu Pro Val
    450                 455                 460

Leu Ile Glu Ile Leu Val Glu Val Met Asp Pro Ser Phe Val Cys Leu
465                 470                 475                 480

Lys Ile Gly Ala Cys Pro Ser Ala His Lys Pro Leu Leu Gly Thr Glu
                485                 490                 495

Lys Cys Ile Trp Gly Pro Ser Tyr Trp Cys Gln Asn Thr Glu Thr Ala
            500                 505                 510

Ala Gln Cys Asn Ala Val Glu His Cys Lys Arg His Val Trp Asn
        515                 520                 525

<210> SEQ ID NO 12
<211> LENGTH: 526
<212> TYPE: PRT
<213> ORGANISM: H. sapiens

<400> SEQUENCE: 12

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95
```

```
Leu Pro Lys Pro Asn Met Ser Ala Ser Cys Lys Glu Ile Val Asp Ser
                100                 105                 110
Tyr Leu Pro Val Ile Leu Asp Ile Ile Lys Gly Glu Met Ser Arg Pro
            115                 120                 125
Gly Glu Val Cys Ser Ala Leu Asn Leu Cys Glu Ser Leu Gln Lys His
        130                 135                 140
Leu Ala Glu Leu Asn His Gln Lys Gln Leu Glu Ser Asn Lys Ile Pro
145                 150                 155                 160
Glu Leu Asp Met Thr Glu Val Ala Pro Phe Met Ala Asn Ile Pro
                165                 170                 175
Leu Leu Leu Tyr Pro Gln Asp Gly Pro Arg Ser Lys Pro Gln Pro Lys
            180                 185                 190
Asp Asn Gly Asp Val Cys Gln Asp Cys Ile Gln Met Val Thr Asp Ile
        195                 200                 205
Gln Thr Ala Val Arg Thr Asn Ser Thr Phe Val Gln Ala Leu Val Glu
210                 215                 220
His Val Lys Glu Glu Cys Asp Arg Leu Gly Pro Gly Met Ala Asp Ile
225                 230                 235                 240
Cys Lys Asn Tyr Ile Ser Gln Tyr Ser Glu Ile Ala Ile Gln Met Met
                245                 250                 255
Met His Met Asp Gln Gln Pro Lys Glu Ile Cys Ala Leu Val Gly Phe
            260                 265                 270
Cys Asp Glu Val Lys Glu Met Pro Met Gln Thr Leu Val Pro Ala Lys
        275                 280                 285
Val Ala Ser Lys Asn Val Ile Pro Ala Leu Glu Leu Val Glu Pro Ile
290                 295                 300
Lys Lys His Glu Val Pro Ala Lys Ser Asp Val Tyr Cys Glu Val Cys
305                 310                 315                 320
Glu Phe Leu Val Lys Glu Val Thr Lys Leu Ile Asp Asn Asn Lys Thr
                325                 330                 335
Glu Lys Glu Ile Leu Asp Ala Phe Asp Lys Met Cys Ser Lys Leu Pro
            340                 345                 350
Lys Ser Leu Ser Glu Glu Cys Gln Glu Val Val Asp Thr Tyr Gly Ser
        355                 360                 365
Ser Ile Leu Ser Ile Leu Leu Glu Glu Val Ser Pro Glu Leu Val Cys
370                 375                 380
Ser Met Leu His Leu Cys Ser Gly Thr Arg Leu Pro Ala Leu Thr Val
385                 390                 395                 400
His Val Thr Gln Pro Lys Asp Gly Gly Phe Cys Glu Val Cys Lys Lys
                405                 410                 415
Leu Val Gly Tyr Leu Asp Arg Asn Leu Glu Lys Asn Ser Thr Lys Gln
            420                 425                 430
Glu Ile Leu Ala Ala Leu Glu Lys Gly Cys Ser Phe Leu Pro Asp Pro
        435                 440                 445
Tyr Gln Lys Gln Cys Asp Gln Phe Val Ala Glu Tyr Glu Pro Val Leu
450                 455                 460
Ile Glu Ile Leu Val Glu Val Met Asp Pro Ser Phe Val Cys Leu Lys
465                 470                 475                 480
Ile Gly Ala Cys Pro Ser Ala His Lys Pro Leu Leu Gly Thr Glu Lys
                485                 490                 495
Cys Ile Trp Gly Pro Ser Tyr Trp Cys Gln Asn Thr Glu Thr Ala Ala
            500                 505                 510
```

```
                Gln Cys Asn Ala Val Glu His Cys Lys Arg His Val Trp Asn
                    515                 520                 525

<210> SEQ ID NO 13
<211> LENGTH: 81
<212> TYPE: PRT
<213> ORGANISM: H. sapiens

<400> SEQUENCE: 13

Ser Leu Pro Cys Asp Ile Cys Lys Asp Val Val Thr Ala Ala Gly Asp
1               5                   10                  15

Met Leu Lys Asp Asn Ala Thr Glu Glu Ile Leu Val Tyr Leu Glu
            20                  25                  30

Lys Thr Cys Asp Trp Leu Pro Lys Pro Asn Met Ser Ala Ser Cys Lys
            35                  40                  45

Glu Ile Val Asp Ser Tyr Leu Pro Val Ile Leu Asp Ile Ile Lys Gly
        50                  55                  60

Glu Met Ser Arg Pro Gly Glu Val Cys Ser Ala Leu Asn Leu Cys Glu
65                  70                  75                  80

Ser

<210> SEQ ID NO 14
<211> LENGTH: 14
<212> TYPE: PRT
<213> ORGANISM: Artificial sequence
<220> FEATURE:
<223> OTHER INFORMATION: Psap peptide

<400> SEQUENCE: 14

Leu Glu Lys Thr Cys Asp Trp Leu Pro Lys Pro Asn Met Ser
1               5                   10

<210> SEQ ID NO 15
<211> LENGTH: 9
<212> TYPE: PRT
<213> ORGANISM: Artificial sequence
<220> FEATURE:
<223> OTHER INFORMATION: Psap peptide

<400> SEQUENCE: 15

Asp Trp Leu Pro Lys Pro Asn Met Ser
1               5

<210> SEQ ID NO 16
<211> LENGTH: 9
<212> TYPE: PRT
<213> ORGANISM: Artificial sequence
<220> FEATURE:
<223> OTHER INFORMATION: Psap peptide

<400> SEQUENCE: 16

Cys Asp Trp Leu Pro Lys Pro Asn Met
1               5

<210> SEQ ID NO 17
<211> LENGTH: 9
<212> TYPE: PRT
<213> ORGANISM: Artificial sequence
<220> FEATURE:
<223> OTHER INFORMATION: Psap peptide

<400> SEQUENCE: 17

Thr Cys Asp Trp Leu Pro Lys Pro Asn
1               5
```

```
<210> SEQ ID NO 18
<211> LENGTH: 9
<212> TYPE: PRT
<213> ORGANISM: Artificial sequence
<220> FEATURE:
<223> OTHER INFORMATION: Psap peptide

<400> SEQUENCE: 18

Lys Thr Cys Asp Trp Leu Pro Lys Pro
1               5

<210> SEQ ID NO 19
<211> LENGTH: 9
<212> TYPE: PRT
<213> ORGANISM: Artificial sequence
<220> FEATURE:
<223> OTHER INFORMATION: Psap peptide

<400> SEQUENCE: 19

Glu Lys Thr Cys Asp Trp Leu Pro Lys
1               5

<210> SEQ ID NO 20
<211> LENGTH: 9
<212> TYPE: PRT
<213> ORGANISM: Artificial sequence
<220> FEATURE:
<223> OTHER INFORMATION: Psap peptide

<400> SEQUENCE: 20

Leu Glu Lys Thr Cys Asp Trp Leu Pro
1               5

<210> SEQ ID NO 21
<211> LENGTH: 9
<212> TYPE: PRT
<213> ORGANISM: Artificial sequence
<220> FEATURE:
<223> OTHER INFORMATION: Psap peptide

<400> SEQUENCE: 21

Asp Trp Leu Pro Lys Pro Asn Met Ser
1               5

<210> SEQ ID NO 22
<211> LENGTH: 9
<212> TYPE: PRT
<213> ORGANISM: Artificial sequence
<220> FEATURE:
<223> OTHER INFORMATION: Psap peptide

<400> SEQUENCE: 22

Cys Asp Trp Leu Pro Lys Pro Asn Met
1               5

<210> SEQ ID NO 23
<211> LENGTH: 9
<212> TYPE: PRT
<213> ORGANISM: Artificial sequence
<220> FEATURE:
<223> OTHER INFORMATION: Psap peptide

<400> SEQUENCE: 23

Thr Cys Asp Trp Leu Pro Lys Pro Asn
1               5
```

```
<210> SEQ ID NO 24
<211> LENGTH: 9
<212> TYPE: PRT
<213> ORGANISM: Artificial sequence
<220> FEATURE:
<223> OTHER INFORMATION: Psap peptide

<400> SEQUENCE: 24

Lys Thr Cys Asp Trp Leu Pro Lys Pro
1               5

<210> SEQ ID NO 25
<211> LENGTH: 9
<212> TYPE: PRT
<213> ORGANISM: Artificial sequence
<220> FEATURE:
<223> OTHER INFORMATION: Psap peptide

<400> SEQUENCE: 25

Glu Lys Thr Cys Asp Trp Leu Pro Lys
1               5

<210> SEQ ID NO 26
<211> LENGTH: 9
<212> TYPE: PRT
<213> ORGANISM: Artificial sequence
<220> FEATURE:
<223> OTHER INFORMATION: Psap peptide

<400> SEQUENCE: 26

Leu Glu Lys Thr Cys Asp Trp Leu Pro
1               5

<210> SEQ ID NO 27
<211> LENGTH: 8
<212> TYPE: PRT
<213> ORGANISM: Artificial sequence
<220> FEATURE:
<223> OTHER INFORMATION: Psap peptide

<400> SEQUENCE: 27

Asp Trp Leu Pro Lys Pro Asn Met
1               5

<210> SEQ ID NO 28
<211> LENGTH: 8
<212> TYPE: PRT
<213> ORGANISM: Artificial sequence
<220> FEATURE:
<223> OTHER INFORMATION: Psap peptide

<400> SEQUENCE: 28

Cys Asp Trp Leu Pro Lys Pro Asn
1               5

<210> SEQ ID NO 29
<211> LENGTH: 8
<212> TYPE: PRT
<213> ORGANISM: Artificial sequence
<220> FEATURE:
<223> OTHER INFORMATION: Psap peptide

<400> SEQUENCE: 29

Thr Cys Asp Trp Leu Pro Lys Pro
1               5
```

```
<210> SEQ ID NO 30
<211> LENGTH: 8
<212> TYPE: PRT
<213> ORGANISM: Artificial sequence
<220> FEATURE:
<223> OTHER INFORMATION: Psap peptide

<400> SEQUENCE: 30

Lys Thr Cys Asp Trp Leu Pro Lys
1               5

<210> SEQ ID NO 31
<211> LENGTH: 8
<212> TYPE: PRT
<213> ORGANISM: Artificial sequence
<220> FEATURE:
<223> OTHER INFORMATION: Psap peptide

<400> SEQUENCE: 31

Glu Lys Thr Cys Asp Trp Leu Pro
1               5

<210> SEQ ID NO 32
<211> LENGTH: 7
<212> TYPE: PRT
<213> ORGANISM: Artificial sequence
<220> FEATURE:
<223> OTHER INFORMATION: Psap peptide

<400> SEQUENCE: 32

Asp Trp Leu Pro Lys Pro Asn
1               5

<210> SEQ ID NO 33
<211> LENGTH: 7
<212> TYPE: PRT
<213> ORGANISM: Artificial sequence
<220> FEATURE:
<223> OTHER INFORMATION: Psap peptide

<400> SEQUENCE: 33

Cys Asp Trp Leu Pro Lys Pro
1               5

<210> SEQ ID NO 34
<211> LENGTH: 7
<212> TYPE: PRT
<213> ORGANISM: Artificial sequence
<220> FEATURE:
<223> OTHER INFORMATION: Psap peptide

<400> SEQUENCE: 34

Thr Cys Asp Trp Leu Pro Lys
1               5

<210> SEQ ID NO 35
<211> LENGTH: 7
<212> TYPE: PRT
<213> ORGANISM: Artificial sequence
<220> FEATURE:
<223> OTHER INFORMATION: Psap peptide

<400> SEQUENCE: 35

Lys Thr Cys Asp Trp Leu Pro
1               5

<210> SEQ ID NO 36
```

```
<211> LENGTH: 6
<212> TYPE: PRT
<213> ORGANISM: Artificial sequence
<220> FEATURE:
<223> OTHER INFORMATION: Psap peptide

<400> SEQUENCE: 36

Asp Trp Leu Pro Lys Pro
1               5

<210> SEQ ID NO 37
<211> LENGTH: 6
<212> TYPE: PRT
<213> ORGANISM: Artificial sequence
<220> FEATURE:
<223> OTHER INFORMATION: Psap peptide

<400> SEQUENCE: 37

Thr Cys Asp Trp Leu Pro
1               5

<210> SEQ ID NO 38
<211> LENGTH: 5
<212> TYPE: PRT
<213> ORGANISM: Artificial sequence
<220> FEATURE:
<223> OTHER INFORMATION: Psap peptide

<400> SEQUENCE: 38

Cys Asp Trp Leu Pro
1               5

<210> SEQ ID NO 39
<211> LENGTH: 4
<212> TYPE: PRT
<213> ORGANISM: Artificial sequence
<220> FEATURE:
<223> OTHER INFORMATION: Psap peptide
<220> FEATURE:
<221> NAME/KEY: MISC_FEATURE
<222> LOCATION: (1)..(1)
<223> OTHER INFORMATION: Acetylated D-amino acid
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (4)..(4)
<223> OTHER INFORMATION: Amidated Pro

<400> SEQUENCE: 39

Asp Trp Leu Pro
1

<210> SEQ ID NO 40
<211> LENGTH: 4
<212> TYPE: PRT
<213> ORGANISM: Artificial sequence
<220> FEATURE:
<223> OTHER INFORMATION: Psap peptide
<220> FEATURE:
<221> NAME/KEY: MISC_FEATURE
<222> LOCATION: (1)..(1)
<223> OTHER INFORMATION: Acetylated Asp
<220> FEATURE:
<221> NAME/KEY: MISC_FEATURE
<222> LOCATION: (4)..(4)
<223> OTHER INFORMATION: Amidated Pro

<400> SEQUENCE: 40
```

Asp Trp Leu Pro
1

<210> SEQ ID NO 41
<211> LENGTH: 4
<212> TYPE: PRT
<213> ORGANISM: Artificial sequence
<220> FEATURE:
<223> OTHER INFORMATION: Psap peptide

<400> SEQUENCE: 41

Asp Trp Ala Pro
1

<210> SEQ ID NO 42
<211> LENGTH: 5
<212> TYPE: PRT
<213> ORGANISM: Artificial sequence
<220> FEATURE:
<223> OTHER INFORMATION: Psap peptide

<400> SEQUENCE: 42

Asp Tyr Leu Pro Lys
1               5

<210> SEQ ID NO 43
<211> LENGTH: 5
<212> TYPE: PRT
<213> ORGANISM: Artificial sequence
<220> FEATURE:
<223> OTHER INFORMATION: Psap peptide

<400> SEQUENCE: 43

Asp Trp Val Pro Lys
1               5

<210> SEQ ID NO 44
<211> LENGTH: 5
<212> TYPE: PRT
<213> ORGANISM: Artificial sequence
<220> FEATURE:
<223> OTHER INFORMATION: Psap peptide

<400> SEQUENCE: 44

Asp Trp Leu Pro Arg
1               5

<210> SEQ ID NO 45
<211> LENGTH: 5
<212> TYPE: PRT
<213> ORGANISM: Artificial sequence
<220> FEATURE:
<223> OTHER INFORMATION: Psap peptide

<400> SEQUENCE: 45

Asp Trp Ala Pro Lys
1               5

<210> SEQ ID NO 46
<211> LENGTH: 4
<212> TYPE: PRT
<213> ORGANISM: Artificial sequence
<220> FEATURE:
<223> OTHER INFORMATION: Psap peptide

<400> SEQUENCE: 46

```
Asp Tyr Leu Pro
1

<210> SEQ ID NO 47
<211> LENGTH: 4
<212> TYPE: PRT
<213> ORGANISM: Artificial sequence
<220> FEATURE:
<223> OTHER INFORMATION: Psap peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: D-amino acid

<400> SEQUENCE: 47

Asp Trp Leu Pro
1

<210> SEQ ID NO 48
<211> LENGTH: 4
<212> TYPE: PRT
<213> ORGANISM: Artificial sequence
<220> FEATURE:
<223> OTHER INFORMATION: Psap peptide
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid

<400> SEQUENCE: 48

Asp Trp Leu Pro
1
```